US012741987B2

(12) United States Patent
Narendran et al.

(10) Patent No.: US 12,741,987 B2
(45) Date of Patent: Sep. 22, 2026

(54) SMALL MOLECULE LIN28 INHIBITORS AS ANTICANCER AGENTS

(71) Applicant: Arumugavadivel Narendran, Calgary (CA)

(72) Inventors: Arumugavadivel Narendran, Calgary (CA); Mohit Jain, Calgary (CA)

(73) Assignee: ARUMUGAVADIVEL NARENDRAN, Calgary (CA)

( * ) Notice: Subject to any disclaimer, the term of this patent is extended or adjusted under 35 U.S.C. 154(b) by 527 days.

(21) Appl. No.: 18/275,678

(22) PCT Filed: Feb. 7, 2022

(86) PCT No.: PCT/CA2022/050170
§ 371 (c)(1),
(2) Date: Aug. 3, 2023

(87) PCT Pub. No.: WO2022/165606
PCT Pub. Date: Aug. 11, 2022

(65) Prior Publication Data

US 2023/0391824 A1 Dec. 7, 2023

Related U.S. Application Data

(60) Provisional application No. 63/146,913, filed on Feb. 8, 2021.

(51) Int. Cl.

| | |
|---|---|
| ***C07K 5/06*** | (2006.01) |
| ***A61K 38/05*** | (2006.01) |
| ***A61K 45/06*** | (2006.01) |
| ***A61P 35/00*** | (2006.01) |
| ***C07K 5/078*** | (2006.01) |
| *A61K 38/00* | (2006.01) |

(52) U.S. Cl.
CPC .......... *C07K 5/06147* (2013.01); *A61K 38/05* (2013.01); *A61K 45/06* (2013.01); *A61P 35/00* (2018.01); *A61K 38/00* (2013.01)

(58) Field of Classification Search
None
See application file for complete search history.

(56) References Cited

FOREIGN PATENT DOCUMENTS

| | | | |
|---|---|---|---|
| WO | 03093498 | A1 | 11/2003 |
| WO | 2009048932 | A2 | 4/2009 |

OTHER PUBLICATIONS

European Patent Application No. 22748776.6, Extended European Search Report dated Dec. 17, 2024.

(Continued)

*Primary Examiner* — Kevin S Orwig

(57) ABSTRACT

LIN28 is an RNA binding protein that binds and inhibits the expression and maturation of let7 microRNA that carries key tumor suppressor functions. Thus, LIN28 is a feasible and effective molecular target for directed inhibition with the potential to provide therapeutic benefit to a diverse group of aggressive malignancies. The present disclosure relates generally to the Rationale, Design, Synthesis and Validation of a Novel Small Molecule Inhibitor of LIN28, coined Compound of formula (I), for the Treatment of Adult and Pediatric Malignancies. In addition, indications of this agent to block cancer metastasis, inhibit cancer stem cells to prevent relapse, and to synergize with immunotherapy, chemotherapy and radiotherapy are also been described.

15 Claims, 30 Drawing Sheets

(56) References Cited

OTHER PUBLICATIONS

European Patent Application No. 22748776.6, Office Action dated Jan. 10, 2025.
Lightfoot et al., "Identification of Small Molecule Inhibitors of the Lin28-mediated Blockage of Pre-let-7g Processing," Organic & Biomolecular Chemistry, Jan. 2016, vol. 14, pp. 10208-10216.
Ambros et al., "Heterochronic Mutants of the Nematode Caenorhabditis Elegans, "Science, Oct. 1984, vol. 226 (4673), pp. 409-416.
Balzeau et al., "The Lin28/let-7 Pathway in Cancer, "Frontiers in Genetics, Mar. 2017, vol. 8, pp. 1-16.
Beachy et al., "Enforced Expression of Lin28b Leads to Impaired T-cell Development, Release of Inflammatory Cytokines, and Peripheral T-cell Lymphoma, "Blood, Aug. 2012, vol. 120(5), pp. 1048-1059.
Chen et al., "Germline Genetic Variants Disturbing the Let-7/lin28 Double-negative Feedback Loop Alter Breast Cancer Susceptibility, "PLOS Genetics, Sep. 2011, vol. 7(9), pp. 1-14.
Chen et al., "Lin28/let-7/PD-L1 Pathway as a Target for Cancer Immunotherapy, "American Association for Cancer Research, Jan. 2019, 31 pages.
Corrigendum: "Genetic Analysis of the Role of the Reprogramming Gene Lin-28 in Human Embryonic Stem Cells, "Stem Cells, 2015, vol. 33(7), pp. 2360-2360.
European Patent Application No. 22748776.6, Office Action dated Oct. 6, 2023.
Faria et al., "Expression of Lin28 and Its Regulatory Micrornas in Adult Adrenocortical Cancer, "Clinical Endocrinology, 2014, pp. 1-8.
Farzaneh et al., "Concise Review: Lin28/let-7 Signaling, a Critical Double-negative Feedback Loop During Pluripotency, Reprogramming, and Tumorigenicity, "Cellular Reprogramming, 2017, vol. 19(5), pp. 1-5.
Feng et al., "Lin28 Regulates Her2 and Promotes Malignancy Through Multiple Mechanisms, "Cell Cycle, Jul. 2012, vol. 11(13), pp. 2486-2496.
Geng et al., "Reduced Let-7f in Bone Marrow-derived Mesenchymal Stem Cells Triggers Treg/Th17 Imbalance in Patients With Systemic Lupus Erythematosus, "Frontiers in Immunology, Feb. 2020, vol. 11, pp. 1-11.
Hamano et al., "High Expression of Lin28 is Associated With Tumour Aggressiveness and Poor Prognosis of Patients in Oesophagus Cancer, "British Journal of Cancer, 2012, vol. 106(8), pp. 1415-1423.
Intemational Patent Application No. PCTCA2022050170, International Preliminary Report on Patentability, dated Aug. 3, 2023.
International Patent Application No. PCT/CA2022/050170 International Search Report and Written Opinion dated Apr. 14, 2022.
Kim et al., "Set7/9 Methylation of the Pluripotency Factor Lin28a is a Nucleolar Localization Mechanism That Blocks Let-7 Biogenesis in Human Escs, "Cell Stem Cell, Dec. 2014, vol. 15(6), pp. 735-749.
Kim et al., "Immunohistochemical Study Identifying Prognostic Biomolecular Markers in Nasopharyngeal Carcinoma Treated by Radiotherapy, "Head Neck, Oct. 2011, vol. 33(10), pp. 1458-1466.
King et al., "Lin28b Promotes Colon Cancer Progression and Metastasis, "Cancer Research, Jun. 2011, vol. 71(12), pp. 4260-4268.
Korshunov et al., "LIN28A immunoreactivity is a potent diagnostic marker of embryonal tumor with multilayered rosettes (ETMR), "Acta Neuropathol, 2012, vol. 124(6), pp. 875-881.
Lee et al., "Lin28b-mediated Expression of Fetal Hemoglobin and Production of Fetal-like Erythrocytes From Adult Human Erythroblasts Ex Vivo, "Blood, Aug. 2013, vol. 122(6), pp. 1034-1041.
Liu et al., "Lin28 Induces Epithelial-to-mesenchymal Transition and Stemness via Downregulation of Let-7a in Breast Cancer Cells, "PLOS One, Dec. 2013, vol. 8(12), pp. 1-13.
Lu et al., "Pluripotent Factor Lin-28 and Its Homologue Lin-28b in Epithelial Ovarian Cancer and Their Associations With Disease Outcomes and Expression of Let-7a and Igf-II, "European Journal Of Cancer, 2009, vol. 45(12), pp. 2212-2218.
Ma et al., "Lin28 Regulates Bmp4 and Functions With Oct4 to Affect Ovarian Tumor Microenvironment, "Cell Cycle, Jan. 2013, vol. 12(1), pp. 88-97.
McCarty., "Metformin May Antagonize Lin28 and/or Lin28b Activity, Thereby Boosting Let-7 Levels and Antagonizing Cancer Progression, "Medical Hypotheses, 2012, vol. 78(2), pp. 262-269.
McDaniel et al., "Lin28 and Let-7: Roles and Regulation in Liver Diseases, "AJP-Gastrointest Liver Physiol, Mar. 2016, vol. 310(10), pp. G757-G765.
Molenaar et al., "Lin28b Induces Neuroblastoma and Enhances Mycn Levels via Let-7 Suppression, "Nature Genetics, Nov. 2012, vol. 44(11), pp. 1199-1206.
Moss et al., "The Cold Shock Domain Protein Lin-28 Controls Developmental Timing in C. Elegans and is Regulated by the Lin-4 Rna, "Cell, Mar. 1997, vol. 88(5), pp. 637-646.
Nam et al., "Molecular Basis for Interaction of Let-7 Micrornas With Lin28, "Cell, 2011, vol. 147(5), pp. 1080-1191.
Nguyen et al., "Lin28 and Let-7 in Cell Metabolism and Cancer, "Translational Pediatrics, 2015, vol. 4(1), pp. 4-11.
Nguyen et al., "Lin28b is Sufficient to Drive Liver Cancer and Necessary for Its Maintenance in Murine Models," Cancer Cell, Aug. 2014, vol. 26(2), pp. 248-261.
Polesskaya et al., "Lin-28 Binds Igf-2 Mrna and Participates in Skeletal Myogenesis by Increasing Translation Efficiency," Genes Development, 2007, vol. 21(9), pp. 1125-1138.
Qin et al., "Lin28 is Involved in Glioma Carcinogenesis and Predicts Outcomes of Glioblastoma Multiforme Patients," Plos One, Jan. 2014, vol. 9(1), pp. 1-11.
Roos et al., "A Small-molecule Inhibitor of Lin28," ACS Chemical Biology, 2016, 9 pages.
Roush et al., "The Let-7 Family of Micrornas," Trends in Cell Biology, 2008, vol. 18(10), pp. 505-516.
Urbach et al., "Lin28 Sustains Early Renal Progenitors and Induces Wilms Tumor," Genes Development, Apr. 2014, vol. 28(9), pp. 1-12.
Viswanathan et al., "Lin28 Promotes Transformation and is Associated With Advanced Human Malignancies," Nature Genetics, Jul. 2009, vol. 41(7), pp. 843-848.
Wang et al., "Lin28 Mediates Radiation Resistance of Breast Cancer Cells via Regulation of Caspase, H2a.x and Let-7 Signaling," Plos One, Jun. 2013, vol. 8(6), pp. 1-6.
Wang et al., "Lin28 Zinc Knuckle Domain is Required and Sufficient to Induce Let-7 Oligouridylation," Cell Reports, Mar. 2017, vol. 18(11), pp. 2664-2675.
Wang et al., "The Pluripotency Factor Lin28b is Involved in Oral Carcinogenesis and Associates With Tumor Aggressiveness and Unfavorable Prognosis," Cancer Cell International, 2015, vol. 15(1), pp. 1-9.
West et al., "A Role for Lin28 in Primordial Germ-cell Development and Germ-cell Malignancy," Nature, Aug. 2009, vol. 460, pp. 909-913.
Wu et al., "Increased Expression of Lin28b Associates With Poor Prognosis in Patients With Oral Squamous Cell Carcinoma," PLOS One, Dec. 2013, vol. 8(12), pp. 1-9.
Xiong et al., "Oncogenic Mechanisms of Lin28 in Breast Cancer: New Functions and Therapeutic Opportunities," Oncotarget, 2017, vol. 8(15), pp. 25721-25735.
Yamoah et al., "Radiation Therapy Intensification for Solid Tumors: a Systematic Review of Randomized Trials," International Journal of Radiation Oncology, Jul. 2015, vol. 93(4), pp. 737-745.
Yuan et al., "Lin28b Reprograms Adult Bone Marrow Hematopoietic Progenitors to Mediate Fetal-like Lymphopoiesis, "Science, Mar. 2012, vol. 335(6073), pp. 1195-1200.
Zhang et al., "Prognostic Value of Lin28a and Lin28b in Various Human Malignancies: a Systematic Review and Meta-analysis, "Cancer Cell International, 2019, vol. 19(1), pp. 1-8.
Zhou et al., "Lin28/Lin28b: An Emerging Oncogenic Driver in Cancer Stem Cells," The International Journal of Biochemistry Cell Biology, 2013, vol. 45(5), pp. 973-978.
Zhu et al., "The Lin28/let-7 Axis Regulates Glucose Metabolism," Cell, Sep. 2011, vol. 147(1), pp. 81-94.
Zhuo et al., "Lin28a Gene Polymorphisms Confer Wilms Tumour Susceptibility: a Four-centre Case-control Study," J Cell Mol Med, 2019, pp. 1-6.

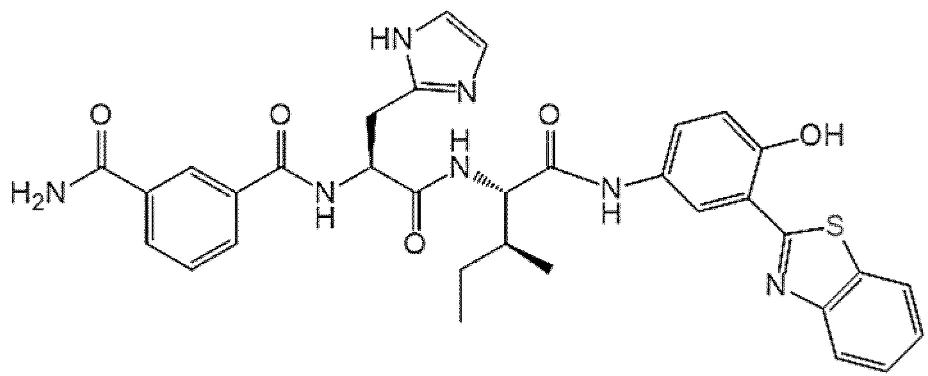

| Chemical formula | $C_{33}H_{33}N_7O_5S$ |
|---|---|
| Molecular weight | 639.73 g/mol |
| Elemental analysis | C, 61.96; H, 5.20; N, 15.33; O, 12.50; S, 5.01 |
| SMILES string | O=C(NC1=CC=C(O)C(C2=NC(C=CC=C3)=C3S2)=C1)[C@H]([C@H](CC)C)NC([C@@H](NC(C4=CC(C(N)=O)=CC=C4)=O)CC5=NC=CN5)=O |

Certificate of Analysis

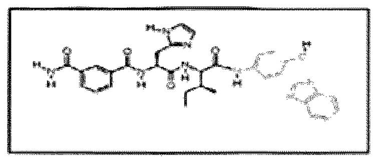

Date: October 08, 2020
Sample/Project Name: Benzothiazole peptide
Lot Number: RPI-010-021PP
Molecular Formula: $C_{33}H_{33}N_7O_5S$
Molecular Weight: 639.72
Quantity Shipped: 20.3 mg
Description: White solid
Purity: >95% by NMR

| Test | Results |
|---|---|
| Melting or Boiling Point: | ND |
| $^1$H NMR Spectrum<br>Mass Spectrum | Consistent<br>Conform with structure |

ND: not determined

FIGURE 4

Effect of Compound of formula (I) on Lin28 protein expression

| | NT-2 | YP-MEL | T47D | BT-12 | WI-38 |
|---|---|---|---|---|---|
| **Lin28A status** | Yes | Yes | Yes | No | No |
| **Lin28B status** | Yes | Yes | No | Yes | No |

FIGURE 8F

YP-MEL cells = Pediatric Neurocutaneous Melanosis (NCM) associated CNS tumor
T47D cells = Adult breast cancer
A549 cells = Adult adenocarcinoma
BT12 cells = Pediatric atypical teratoid rhabdoid tumor (AT/RT)

YP-MEL tumors in vivo (I.P. treatment, 4mg/kg Compound of formula (I) (P1 isomer)

NT-2 testicular tumor xenografts treated with 4 mg/kg Compound of formula (I) (isomer P1) via oral route of administration (P.O) in SCID mice

NT-2 testicular tumor xenografts treated with 4 mg/kg Compound of formula (I) (isomer P1) via oral route of administration (P.O) in SCID mice

I.P. treated NT-2 testicular tumors 4mg/kg Compound of formula (I)

NT-2 tumor bearing SCID mice treated with 4mg/kg Compound of formula (I) intraperitoneally (I.P)

Male SCID NT-2 tumor bearing mice treated with 4mg/kg Compound of formula (I) I.V. Total of 4 Treatments [Vehicle/Control group = 0.1% DMSO in PBS]

OpenVnmrJ

Recorded on: mr400, Feb 10 2021
Pulse Sequence: PRESAT
Sweep Width(Hz): 4807.69
Digital Res.(Hz/pt): 0.07
Acquisition Time(s): 5
Hz per mm(Hz/mm): 6.38
Relaxation Delay(s): 0.1
Completed Scans: 4

RPI-010-76-P1
399.980 MHz H1 1D in dmso (ref. to DMSO @ 2.49 ppm)
temp 25.9 C -> actual temp = 27.0 C, onenmr probe OpenVnmrJ Recorded on: mr400, Feb 9 2021 Sweep Width(Hz): 4807.69 Acquisiton Time(s): 5 Relaxation Delay(s): 0.1
Pulse Sequence: PRESAT Digital Res.(Hz/pt): 0.07 Hz per mm(Hz/mm): 5.69 Completed Scans: 4

RPI-010-76-P2
399.980 MHz H1 1D in dmso (ref. to DMSO @ 2.49 ppm)
temp 25.9 C -> actual temp = 27.0 C, onenmr probe File: /mnt/d600/home10/ranepha/nmrdata/2021.02.09.nv4_RPI-010-76-P2_H1_PRESAT

SMALL MOLECULE LIN28 INHIBITORS AS ANTICANCER AGENTS

CROSS REFERENCE TO RELATED APPLICATION

This application claims priority to U.S. provisional patent application U.S. 63/146,913, filed Feb. 8, 2021, the entire contents of which is hereby incorporate by reference.

FIELD

The present disclosure relates generally to the Rationale, Designing, Synthesis and Validation of a Novel Small Molecule Inhibitor Anticancer Agent.

BACKGROUND

The LIN28 family of proteins is a group of developmentally regulated proteins that exert their physiological and oncogenic functions through their capacity to interact with distinct cellular regulatory RNAs. LIN28 was initially discovered through mutagenesis screens of modulators of developmental timing in *Caenorhabditis elegans* (*C. elegans*) [1]. These proteins are made of zinc fingers and RNA binding domains [2]. Mammalian cells carry the genomic information for two homologues for the lin28 gene named LIN28A and LIN28B and express the corresponding proteins. Functionally, these genes have been shown to alter both normal and pathogenic cellular functions through distinct mechanisms. These include, (a) interaction with critical mRNAs and the regulation of their stability and translation, (b) binding to the precursors of distinct microRNAs (miRNAs) to prevent of their expression and maturation processes.

Normal physiological functions of LIN28 proteins include participation in a wide range of normal cellular functions including glucose metabolism, lymphopoiesis, skeletal myogenesis and germ cell development [3-6]. Importantly, a critical function of LIN28 in the regulation of embryonic stem cell maturation has been demonstrated and studies have shown that LIN28 participates in the cellular events that lead to the reprogramming of somatic cells that lead to the generation of pluripotent stem cells [7].

There is strong evidence to implicate LIN28 family of molecules in cancer formation and growth. Previous studies have demonstrated abnormal and cancer specific expression of LIN28A and LIN28B in wide range of tumor specimens [8]. In vivo animal models have also confirmed that the ectopic expression of LIN28 is sufficient to step up tumor growth [9]. It has also been shown that the inhibition of LIN28 by siRNA leads to the regression of human tumor xenografts containing the gene [10]. Furthermore, genomic studies in animal models have also shown that the reactivation of LIN28A/B can push cancer initiation and progression by let-7 dependent and independent pathways [11]. LIN28A/B mediated reprogramming of cell metabolism has been shown to be one of the potential mechanisms for the oncogenic effects induced in these cells [11].

The second line of evidence for a role of LIN28 in tumorigenesis comes from the observation that LIN28 has been shown to bind and block the maturation and subsequent inactivation of the important tumor suppressor microRNA (miRNA) let-7 [12]. The loss of activity of let-7 leads to the activation of multiple oncogenes resulting in tumor formation and growth [13]. Multiple recent research studies have shown that the down regulation of let-7 may pave the way for the formation of many tumors and conversely it's down regulation or inactivation has the potential to impede cancer growth [14]. Mechanistically, it has been demonstrated that LIN28 binds to the immature form of let-7 and prevents its post-transcriptional processing by small-RNA generating mechanisms in the nucleus [15]. Furthermore, in the cytoplasm, loading of the premature form of let-7 into Dicer is blocked by LIN28 binding which initiates the recruitment of pathways for its subsequent degradation [11, 16]. Consequently, when interacted by Lin28, let-7 is made inactive allowing the associated oncogenic developments to proceed.

In addition, and importantly, LIN28 genes have the capacity to function as oncogenes themselves and to advance malignant transformation of normal cells. Overall, the tumors that have been found to be associated with LIN28A/B mutations include, but not limited to, breast cancer [17, 18], ovarian cancer [19, 20], colon cancer [21], adrenocortical cancers [22], hepatic malignancies [23], squamous cell carcinoma [24, 25], head and neck cancers [26], esophageal cancer [27], glioblastoma multiforme [28] as well as the mostly pediatric tumors such as neuroblastoma [29], embryonal tumor with multilayered rosettes (ETMR) [30] and Wilms tumor [31]. Increased LIN28 has also been shown to enable aggressive cancer properties including increased metastasis [21]. A study by Beachy et al. has shown that increased expression of LIN28B results in altered T-cell development and the release of potentially tumor promoting inflammatory cytokines [32].

Clinically, an association between the expression and abnormal activity of LIN28 and outcomes has also been reported. A meta-analysis by Zhang and colleagues has shown LIN28A overexpression was significantly related to patient outcomes including overall survival (OS) and disease-free survival (DFS) [14]. Furthermore, the analyses of clinical epidemiological data also show that, in particular types of malignancies, the susceptibility to tumor development is associated with LIN28 aberrations [33].

Targeting LIN28 carries many important implications for the development of effective cancer therapeutics. Many of the current conventional anticancer treatment target the bulk of the tumor but carry very little effect of cancer stem cells (CSC). It has been well established that the inability to eliminate CSC is a critical mechanism for cancer relapse. Studies have shown the expression of LIN28 as a key characteristic in many tumors suggesting its contribution to the stemness of these cells [34]. A number of reports have shown the key contribution of the LIN28A/B and let-7 axis in the control of self-renewal and differentiation of stem cells. Thus, LIN28 targeting agents have the potential to be effective therapeutic agents with lower treatment failures. Furthermore, such agents can also be used to overcome resistance to many of the current treatment approaches including chemotherapy and radiotherapy as LIN28A/B has been directly implicated in the generation of resistance to these treatments [9].

During human development, during the final stages of fetal maturation and in early infancy, the hemoglobin in red blood cells switch from fetal hemoglobin (HbF) to adult type hemoglobin (HbA). Alterations in HbF levels play and important role in the pathogenesis and clinical symptoms of a number of related diseases. LIN28 has been shown to play a regulatory function in this process by enhancing the fetal-like phenotype [35]. For this purpose, agents such as the one described herein will be used in the treatment of diseases where an increase in HbF has been demonstrated. These diseases include; Fanconi anemia, Dyskeratosis Congenita, Diamond-Blackfan syndrome, Erythroleukemia, Juvenile Chronic Myeloid Leukemia and Thalassemia.

SUMMARY

In one aspect there is provided a compound of Formula (I), or a tautomer, or a pharmaceutically acceptable salt, or a solvate, or a functional derivative thereof:

(I)

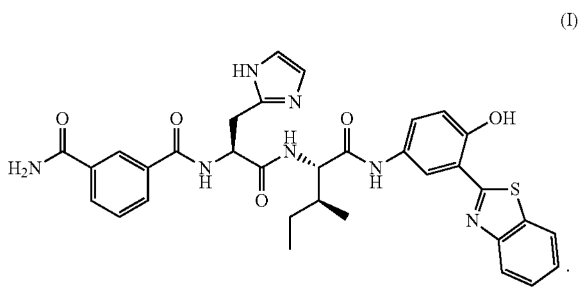 [SMILES: CC[C@H](C)[C@H](NC(=O)[C@H](Cc1ncc[nH]1)NC(=O)c1cccc(C(N)=O)c1)C(=O)Nc1ccc(O)c(-c2nc3ccccc3s2)c1]

In one aspect there is provided a compound of Formula (I), or a pharmaceutically acceptable salt, or a solvate, or a functional derivative thereof:

(I)

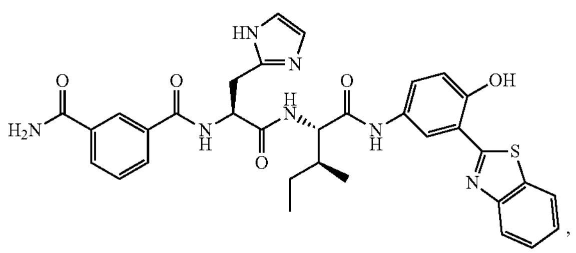

comprising a tautomer of Formula (P1)

(P1)

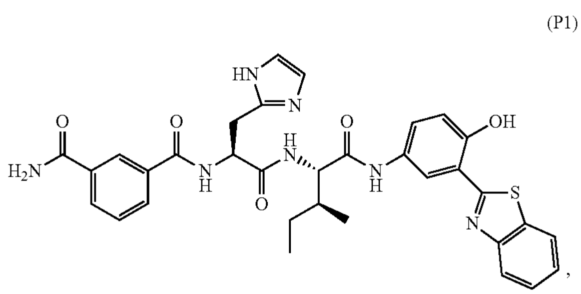 [SMILES: CC[C@H](C)[C@H](NC(=O)[C@H](Cc1ncc[nH]1)NC(=O)c1cccc(C(N)=O)c1)C(=O)Nc1ccc(O)c(-c2nc3ccccc3s2)c1]

and/or a tautomer of Formula P2

(P2)

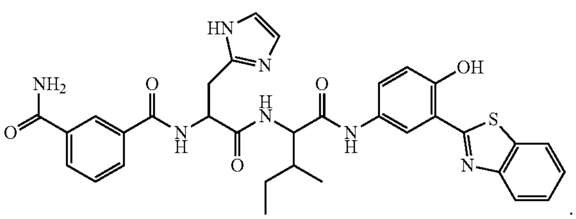

In one example, the compound of Formula (I) comprises a tautomer of Formula (P1)

(P1)

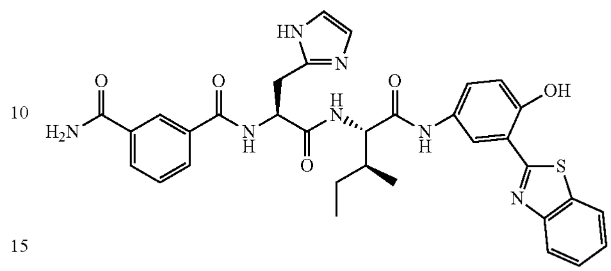

In one example, the compound of Formula (I) comprises a tautomer of Formula (P2)

(P2)

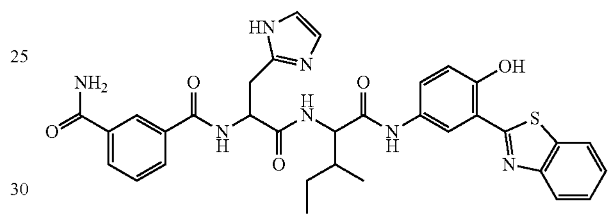

In one aspect there is provided a compound of Formula (I-B), or a tautomer, or a pharmaceutically acceptable salt, or a solvate, or a functional derivative thereof:

(I-B)

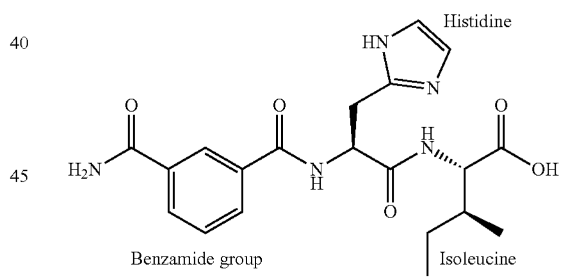

In one aspect there is provided a composition comprising a compound of any one of claims 1 to 5, and a pharmaceutically acceptable carrier, diluent, or vehicle.

In one aspect there is provided a method of treating a subject with cancer, at risk of developing cancer, or suspected of having a cancer, comprising: administering a therapeutically effective amount of a compound of any one of claims 1 to 5, or a composition of claim 6.

In one example, the cancer is Acute Myeloid Leukemia (AML), Atypical teratoid/rhabdoid tumor, Embryonal tumors with multi-layered rosettes [ETMR], Brain cancers (Pediatric and adult), Breast cancer, Cervical cancer, Sarcomas, Chronic myeloid leukemia (CML), Colon cancer, Gastric cancer, Germ cell tumors, Yolk sac tumors, gastric cancer, Oesophageal cancer, rectal cancers, Glioblastoma multiforme, Glioma (pediatric and adult), Liver cancer, Medulloblastoma, Multiple Myeloma, Neuroblastoma, Oral squamous cell carcinoma, Ovarian primitive germ cell tumors, Ovarian cancer (Epithelial) cancers, Pheochromocytomas, Paragangliomas, Primitive neuroectodermal tumors, Prostate cancer, Testicular germ cell tumors, Wilms tumor, Pediatric neurocutaneous melanosis (NCM) associated CNS tumor, adenocarcinoma, or testicular cancer.

In one example, the subject a pediatric subject or an adult subject.

In one example, the subject is a human.

In one example, the cells of said cancer overexpresses LIN28A protein and/or LIN28B protein, optionally compared to a control.

In one example, the cells of said cancer comprise reduced levels let-7 microRNA, optionally compared to a control.

In one example, the LIN28A gene and/or LIN28B gene within said cells of said cancer comprise mutations and/or or SNPs amplifications.

In one example, the cancer is resistant to chemotherapy and/or radiation therapy.

In one example, further comprising treatment with radiation therapy.

In one example, further comprising treatment with a chemotherapeutic agent

In one example, said chemotherapeutic agent is one or more of Antimetabolites (Methotrexate, Cytarabine, 5-fluorouracil, gemcitabine, 6-mercaptopurine, Fludarabine, Cladarabine and Hydroxyurea), Alkylating agents (Cyclophophamide, Ifosphamide, Chlorambucil, Melphalan, Temozolamide, Cisplatin, Carboplatin, Oxaliplatin) Topoisomerase inhibitors (Irinotecan, Topotecan, Etoposide, Teniposide) Mitotic inhibitors (Vincristine, Vinblastine, Vinorelbine, Docetaxel, Paclitaxel), Antibiotics (Bleomycin, Actinomycin D, Doxorubicin, Daunorubicin, Idarubicin), Protein kinase inhibitors (Imatinib, Dasatinib, Nilotinib, Erlotinib, Gefitinib, crizotinib, Dabrafenib, Vemurafenib, Trametinib), Enzymes (L-Asparaginase), Proteasome inhibitors (Bortezomib, Carfilzomib), Monoclonal antibodies (trastuzumab, bevacizumab, rituximab)

In one example, further comprising treatment with an immunotherapy checkpoint inhibitor.

In one aspect there is provided a use of a therapeutically effective amount of a compound of any one of claims 1 to 5, or a composition of claim 6, for treating a subject with cancer, at risk of developing cancer, or suspected of having a cancer.

In one aspect there is provided a use of a therapeutically effective amount of a compound of any one of claims 1 to 5, or a composition of claim 6, in the manufacture of a medicament for treating a subject with cancer, at risk of developing cancer, or suspected of having a cancer.

In one example, the cancer is Acute Myeloid Leukemia (AML), Atypical teratoid/rhabdoid tumor, Embryonal tumors with multi-layered rosettes [ETMR], Brain cancers (Pediatric and adult), Breast cancer, Cervical cancer, Sarcomas, Chronic myeloid leukemia (CML), Colon cancer, Gastric cancer, Germ cell tumors, Yolk sac tumors, gastric cancer, Esophageal cancer, rectal cancers, Glioblastoma multiforme, Glioma (pediatric and adult), Liver cancer, Medulloblastoma, Multiple Myeloma, Neuroblastoma, Oral squamous cell carcinoma, Ovarian primitive germ cell tumors, Ovarian cancer (Epithelial) cancers, Pheochromocytomas, Paragangliomas, Primitive neuroectodermal tumors, Prostate cancer, Testicular germ cell tumors, Wilms tumor, Pediatric neurocutaneous melanosis (NCM) associated CNS tumor, adenocarcinoma, or testicular cancer.

In one example, the subject a pediatric subject or an adult subject.

In one example, the subject is a human.

In one example, the cells of said cancer overexpresses LIN28A protein and/or LIN28B protein, optionally compared to a control.

In one example, the cells of said cancer comprise reduced levels let-7 microRNA, optionally compared to a control.

In one example, the LIN28A gene and/or LIN28B gene within said cells of said cancer comprise mutations and/or or SNPs amplifications.

In one example, the cancer is resistant to chemotherapy and/or radiation therapy.

In one example, further comprising use of radiation therapy.

In one example, further comprising use of a chemotherapeutic agent

In one example, said chemotherapeutic agent is one or more of Antimetabolites (Methotrexate, Cytarabine, 5-fluorouracil, gemcitabine, 6-mercaptopurine, Fludarabine, Cladarabine and Hydroxyurea), Alkylating agents (Cyclophophamide, Ifosphamide, Chlorambucil, Melphalan, Temozolamide, Cisplatin, Carboplatin, Oxaliplatin) Topoisomerase inhibitors (Irinotecan, Topotecan, Etoposide, Teniposide) Mitotic inhibitors (Vincristine, Vinblastine, Vinorelbine, Docetaxel, Paclitaxel), Antibiotics (Bleomycin, Actinomycin D, Doxorubicin, Daunorubicin, Idarubicin), Protein kinase inhibitors (Imatinib, Dasatinib, Nilotinib, Erlotinib, Gefitinib, crizotinib, Dabrafenib, Vemurafenib, Trametinib), Enzymes (L-Asparaginase), Proteasome inhibitors (Bortezomib, Carfilzomib), Monoclonal antibodies (trastuzumab, bevacizumab, rituximab)

In one example, further comprising use of an immunotherapy checkpoint inhibitor.

In one aspect there is provided a kit, comprising a compound of any one of claims 1 to 5, or a composition of claim 6, a container, and optionally instructions for the use there of.

BRIEF DESCRIPTION OF THE FIGURES

Embodiments of the present disclosure will now be described, by way of example only, with reference to the attached Figures.

The deprotection of Trityl was achieved separately to obtain P1 and P2 isomers. The one-sided arrow in the P2 isomer shows the rotation or inter-substitution of benzamide associated amine and carbonyl functional groups. This molecular re-arrangement of P2 isomer may have led to subsequent modification of 3D conformation, potentially causing a reduced exposure of its solvent accessible surfaces. The presence of these purified isomers were analytically confirmed using Nuclear Magnetic Resonance (NMR) and Mass Spectrometry.

FIG. 4: Compound of formula (I) structure and elemental composition.

Figure 5:
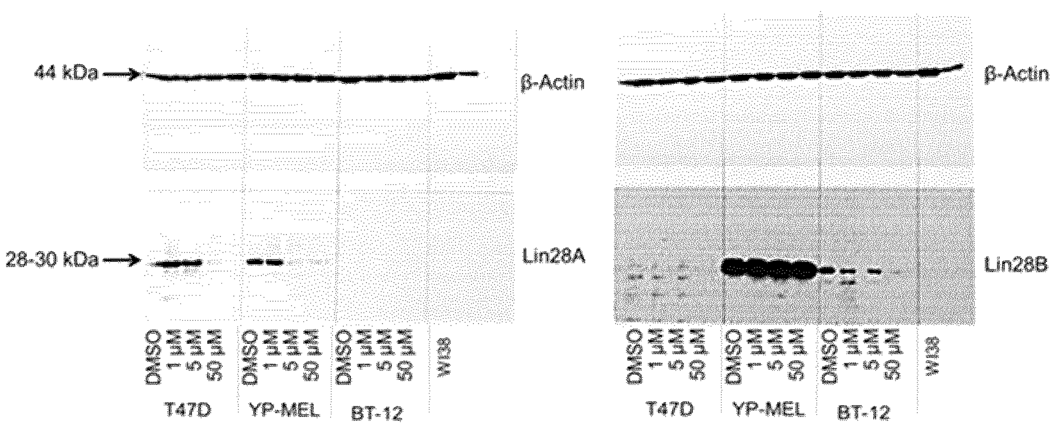

FIG. 5: Compound of formula (I) mixture, containing the two isomers (P1+P2) causes significant reduction in Lin28A protein from 5 μM onwards, in a panel of endogenously LIN28 expressing cancer cell models. This novel molecule inhibits LIN28B at 50 μM, demonstrating 10-fold binding differential between its affinity for LIN28A relative to LIN28B. LIN28A and LIN28B expression profile in pediatric CNS cancer cell lines, 96-hr post-treatment with Compound of formula (I). SDS-PAGE on 10% polyacrylamide gel of total cell lysates from untreated cells harvested at 80-90% confluency. Samples loaded with volumes for 20 μg protein. LIN28A and LIN28B proteins were detected using the anti-LIN28A antibody (#8706; Cell Signaling Technology) and anti-LIN28B antibody (#11965; Cell Signalling Technology) at 1:2000 dilutions. T47D: adult breast cancer (LIN28A expressing); YPMEL: malignant melanoma derived from Neurocutaneous Melanosis (NCM) (Lin28A and Lin28B expressing); BT-12: pediatric atypical-teratoid rhabdoid tumor (AT/RT).

Figure 6:
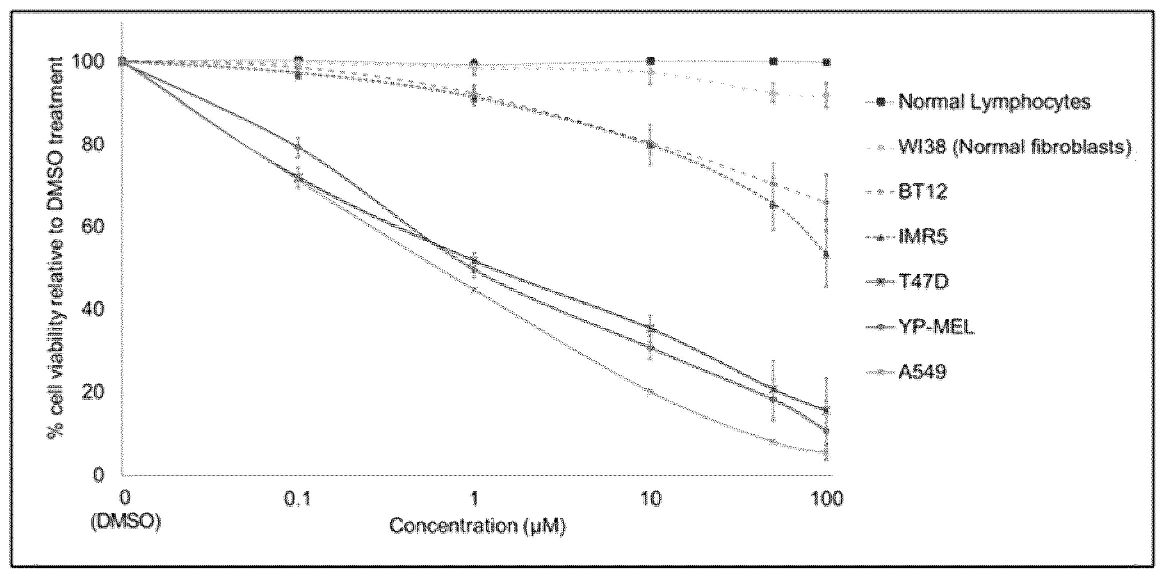

FIG. 6: Cells were cultured in the presence of the Compound of formula (I) (P1+P2) at increasing concentrations and cell viability was evaluated using Alamar Blue dye and measurement at Excitation of 550 nm and Emission of 590 nm. All the data shown are representative of three replicates. LIN28A-positive cancer cell models displayed heightened sensitivity to Compound of formula (I), relative to LIN28B-expressing cancer cell models. Whereas, normal lymphocytes and fibroblast cells (LIN28-negative) lacked sensitivity to Compound of formula (I) at treated dosages, over 96-120 hour. IC50 concentrations of Compound of formula (I) in panel of cancer cell lines expressing Lin28A ranged at ≤1 μM (cell lines A549, YP-MEL, T47D), where cancer cells expressing only Lin28B demonstrated IC50 at 100 μM (cell lines IMR5 and BT12). LIN28A and LIN28B expression in the presence of Compound of formula (I) correlates with the sensitivity of cells to this inhibitor.

Figures 7A, 7B, 7C:
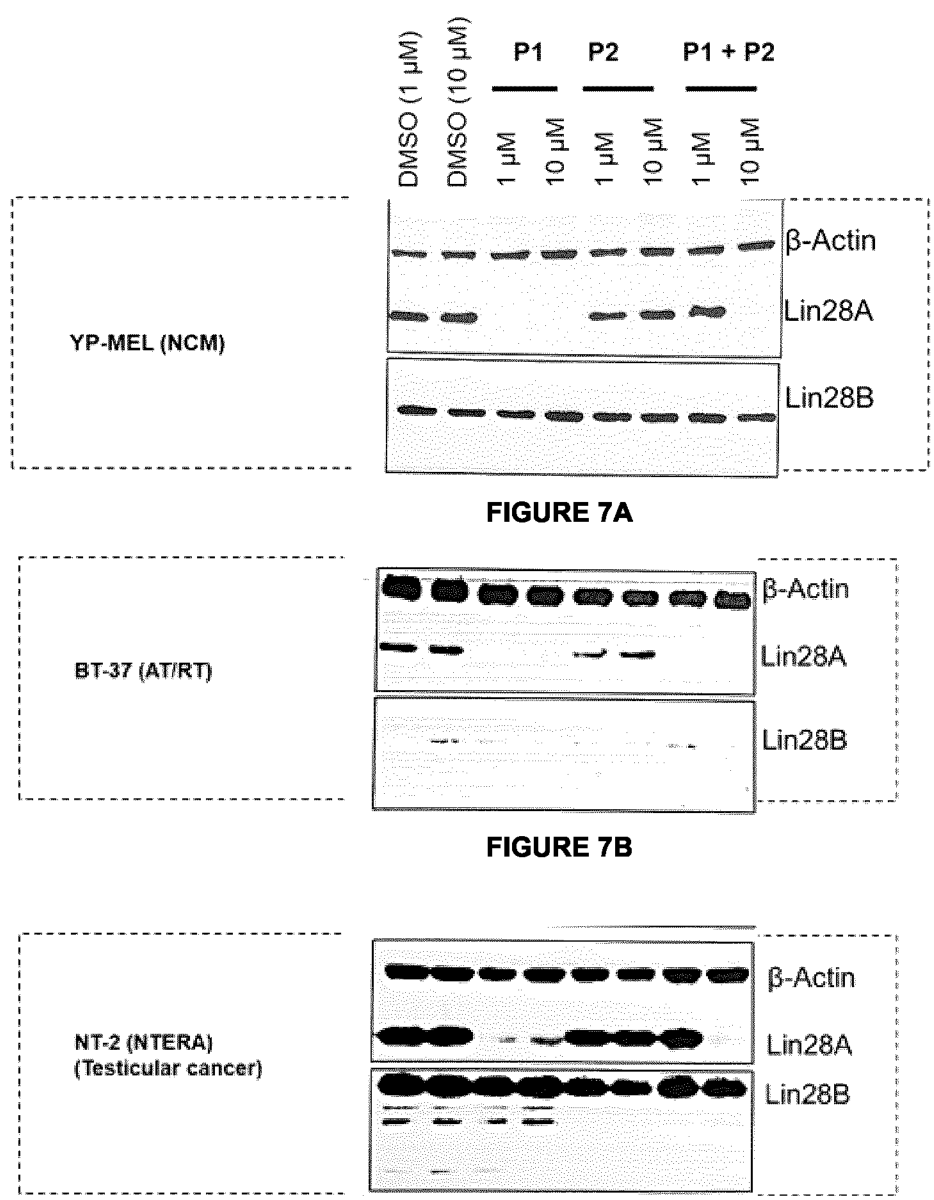
Figure 8A:
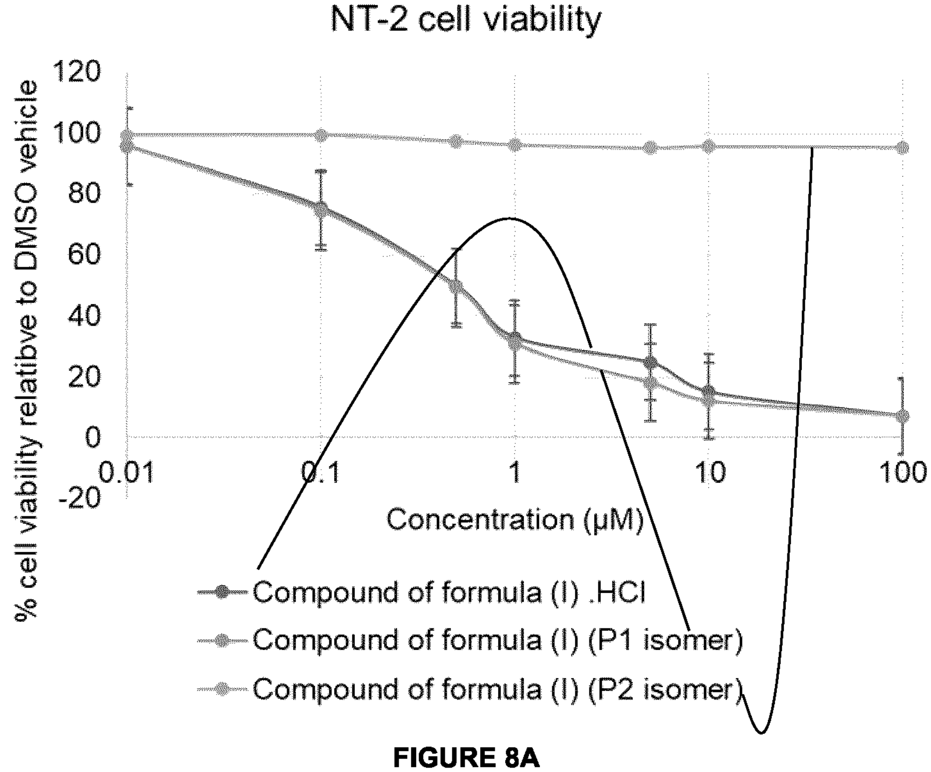
Figure 8B:
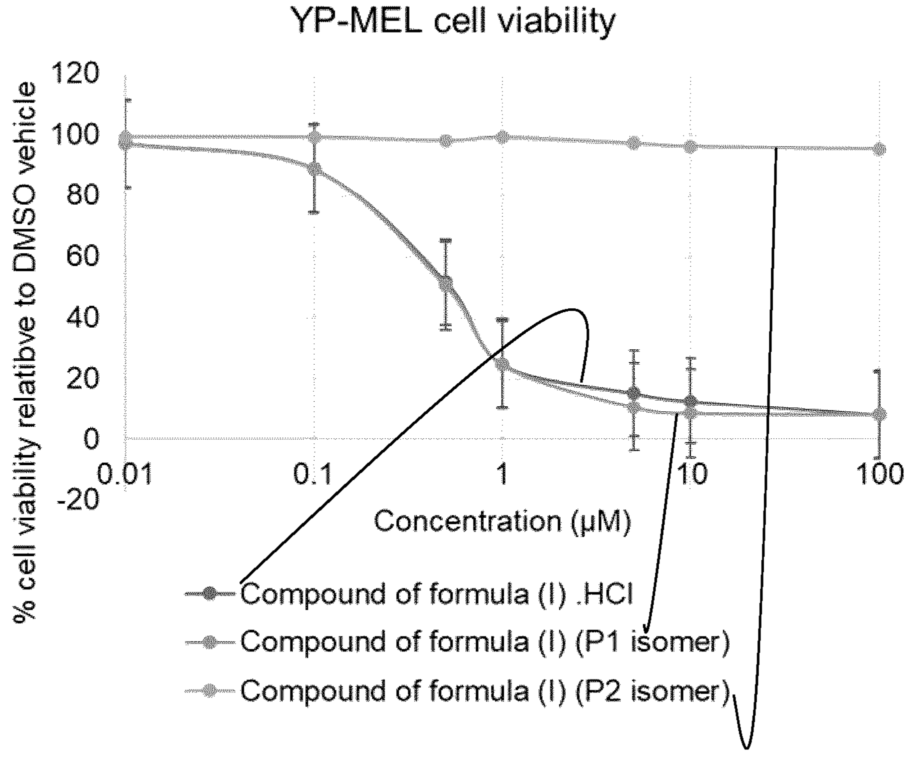
Figure 8C:
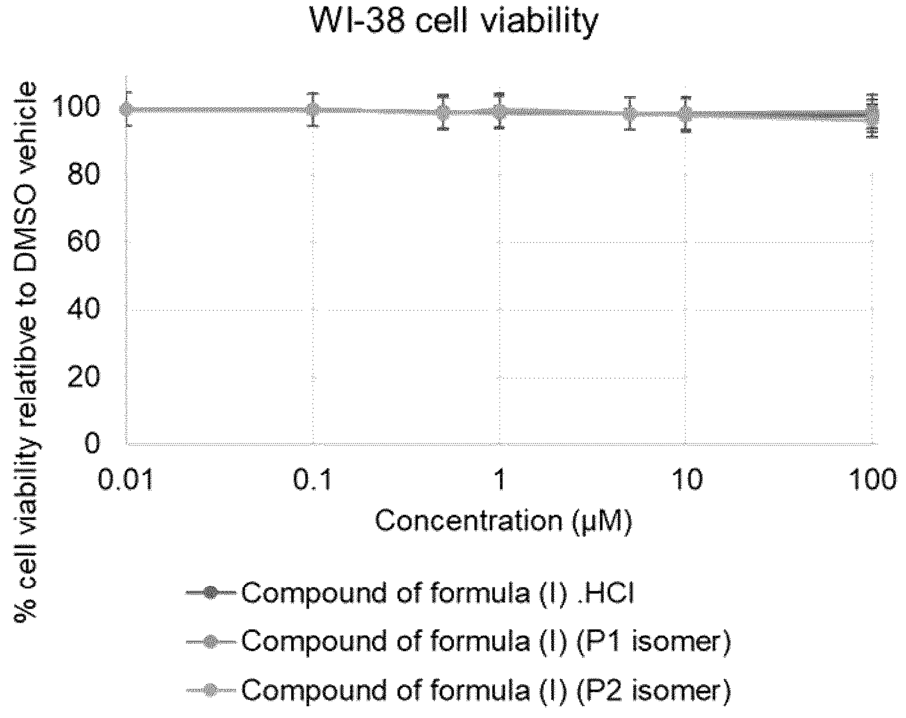
Figure 8D:
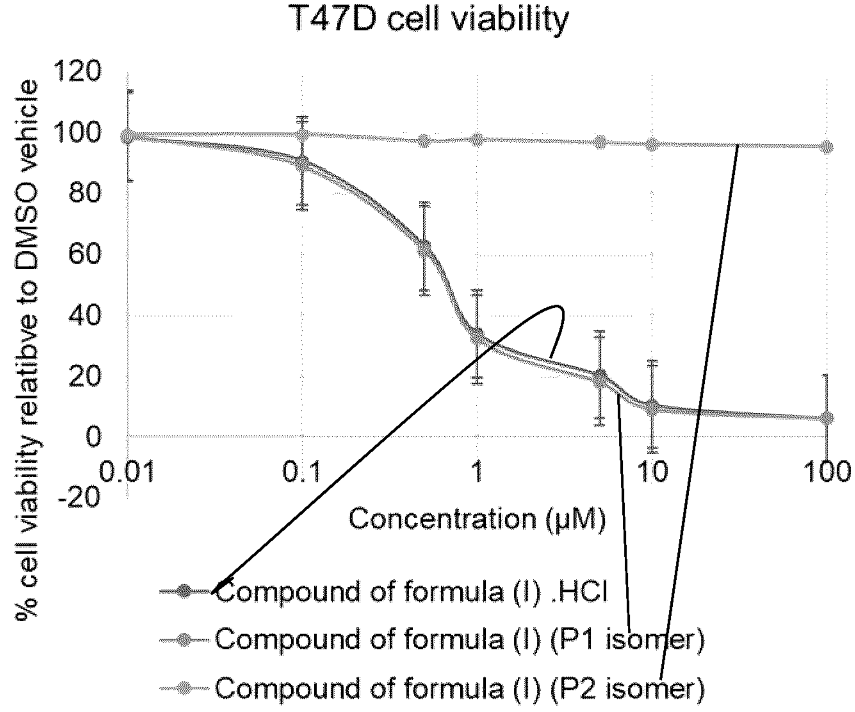
Figure 8E:
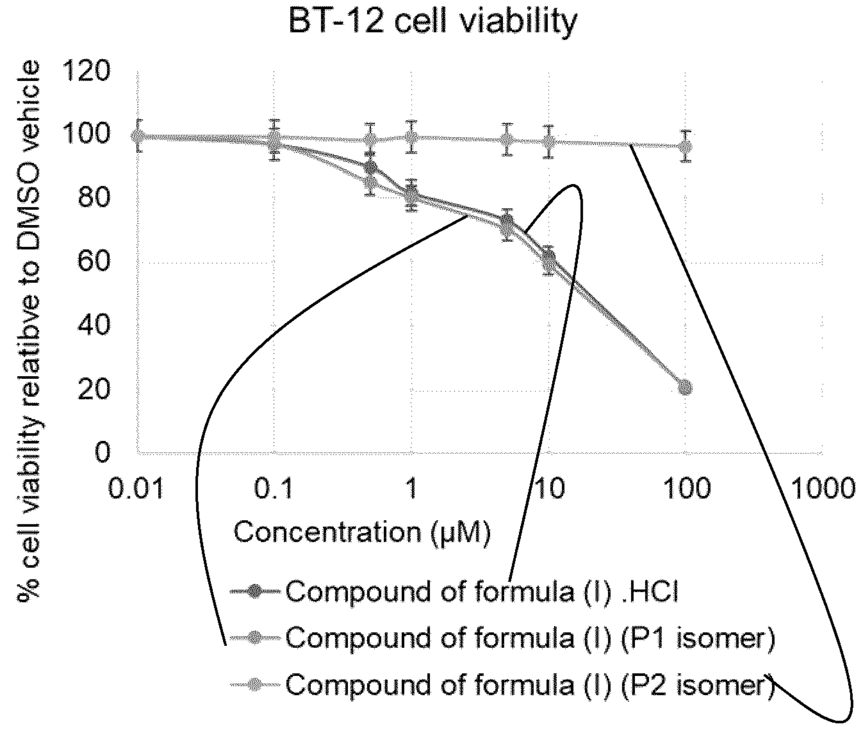

FIG. 7A-C: To determine the differences in the biological activity of the two isomers (P1+P2) of Compound of formula (I), we tested the effects of purified and separated P1 and P2 isomers on the protein expression of Lin28A and Lin28B. (A) YP-MEL (NCM). (B) BT-37 (AT/RT). (C) NT-2 (NTERA) (Testicular cancer). The western blotting of NCM, AT/RT and testicular cells for Lin28 proteins demonstrated that the most soluble (soluble until 100 mg/ml in DMSO) version of Compound of formula (I) called P1 was capable of inhibiting Lin28A selectively from 1 μM onwards whereas, the less soluble version P2 (insoluble at 1 mg/ml in DMSO) had no effect on the expression levels of Lin28A in the tested cell models. Lin28B expression remained unaltered from the treatments of P1 and P2 at the tested dosages. It was noted that the P1 version of Compound of formula (I) was 5 times more selective that the crude mixture containing P1+P2, as observed in FIG. 5.

FIG. 8A-F: Cells were cultured in the presence of the Compound of formula (I) (versions P1, P2 or P1+P2 at equipotent doses) at increasing concentrations and cell viability was evaluated using Alamar Blue dye and measurement at Excitation of 550 nm and Emission of 590 nm. All the data shown are representative of three replicates. LIN28A-positive cancer cell models displayed heightened sensitivity to Compound of formula (I), relative to LIN28B-expressing cancer cell models. A. NT-2 cell viability. B. YP-MEL cell viability. C. WI-38 cell viability. D. T47D cell viability. E. BT-12 cell viability. F. summary of Lin28A and Lin28B status.

Figure 9:
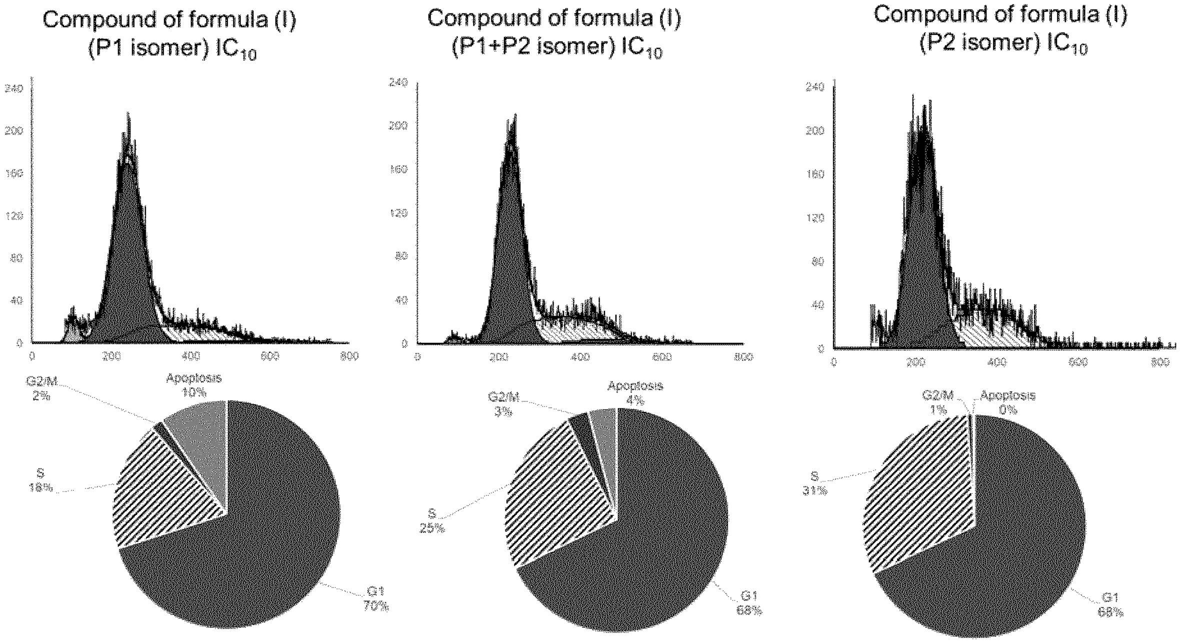

FIG. 9: NT-2, testicular cancer cells, were incubated with Compound of formula (I) isomers for 24h and subjected to Flow Cytometric analysis to determine the alterations in cancer cell cycle. In the first 24h, the P1 version of Compound of formula (I) triggered apoptosis in NT-2 testicular cancer cells where approximately 10% of the total cell count had undergone cell death This finding further proved the effectiveness of isomer P1 in causing cancer cell death. As expected, the P1+P2 version was only half as effective in triggering cancer cell death. P2, however, failed to cause any significant changes in cancer cell viability. Therefore, only the P1 isomer of Compound of formula (I) was investigated further to determine its in vitro and in vivo efficacy.

Figure 10:
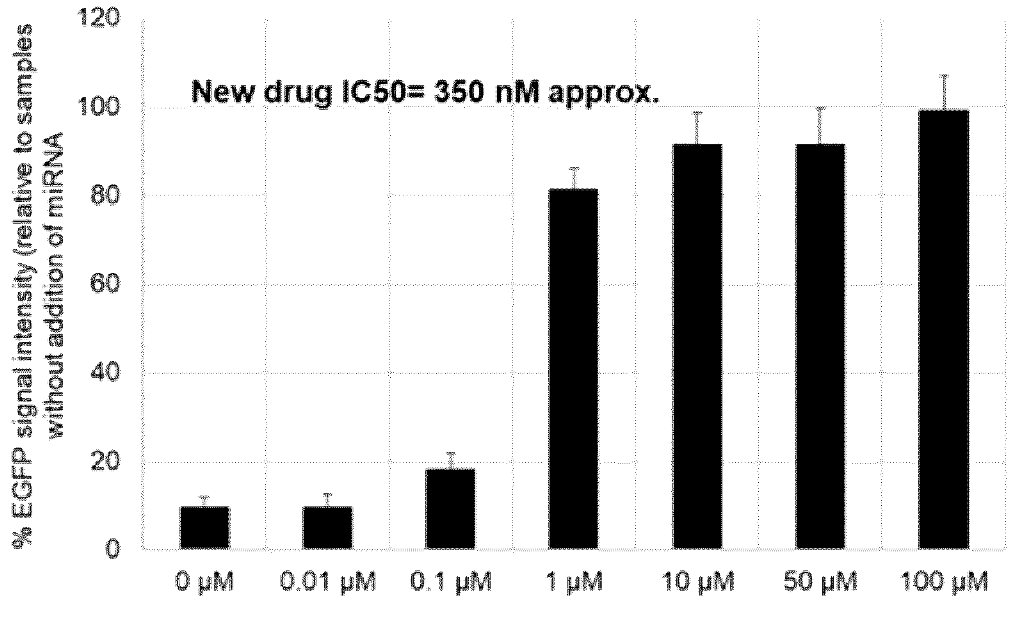
Figure 11:
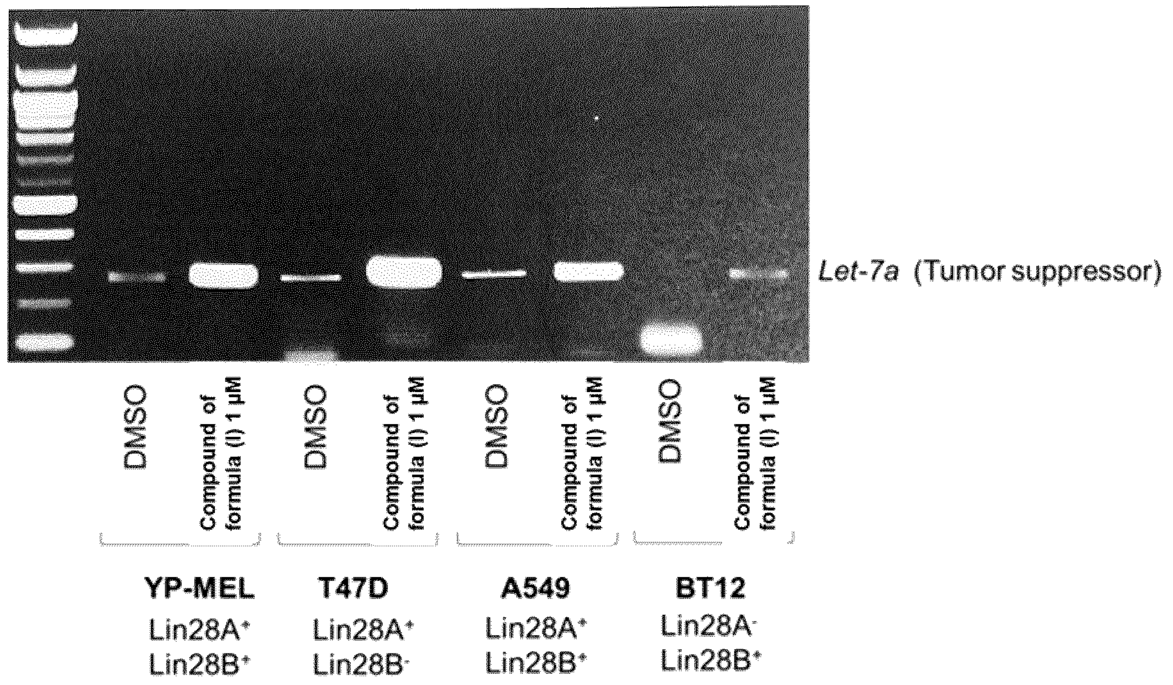

FIG. 10: FRET optimization of BHQ1-tagged pre-let-7a [19B-let7a] (acceptor) mediated concentration-dependent quenching of EGFP-tagged Lin28A (donor). 19B-let7a at 100 nM, displayed 90% quenching of EGFP-lin28A and was chosen for FRET screening with P1 ver. The introduction of Compound of formula (I) resulted in a dose-dependent displacement of recombinant BHQ1-pre-let7a and EGFP-Lin28A bound complexes displaying a reduction in FRET by 70% at 1 μM as compared to c1632, a known pan-Lin28 inhibitor, which displayed equivalent FRET reduction at 100 μM FIG. 11: Compound of formula (I) lead to successful rescue of pre-Iet-7a and their maturation to miRNA let-7a tumor suppressor, only at 1 μM. Pharmacological inhibition of Lin28A using Compound of formula (I) lead to increase in the expression of let-7a miRNA tumor suppressor (Taqman MicroRNA Assay: has-let-7a: 000377) in YP-MEL, T47D, A549 (Adult adenocarcinoma; both LIN28A and LIN28B expressing) cells, measured by Taqman miRNA qRT-PCR. Whereas, Lin28B expressing BT-12 demonstrated only minor upregulation of let-7a suggesting a therapeutic concentration window between the preference of Compound of formula (I) for Lin28A versus Lin28B Change in miRNA expression levels were relative to noncoding RNU6B.

Figure 12A:
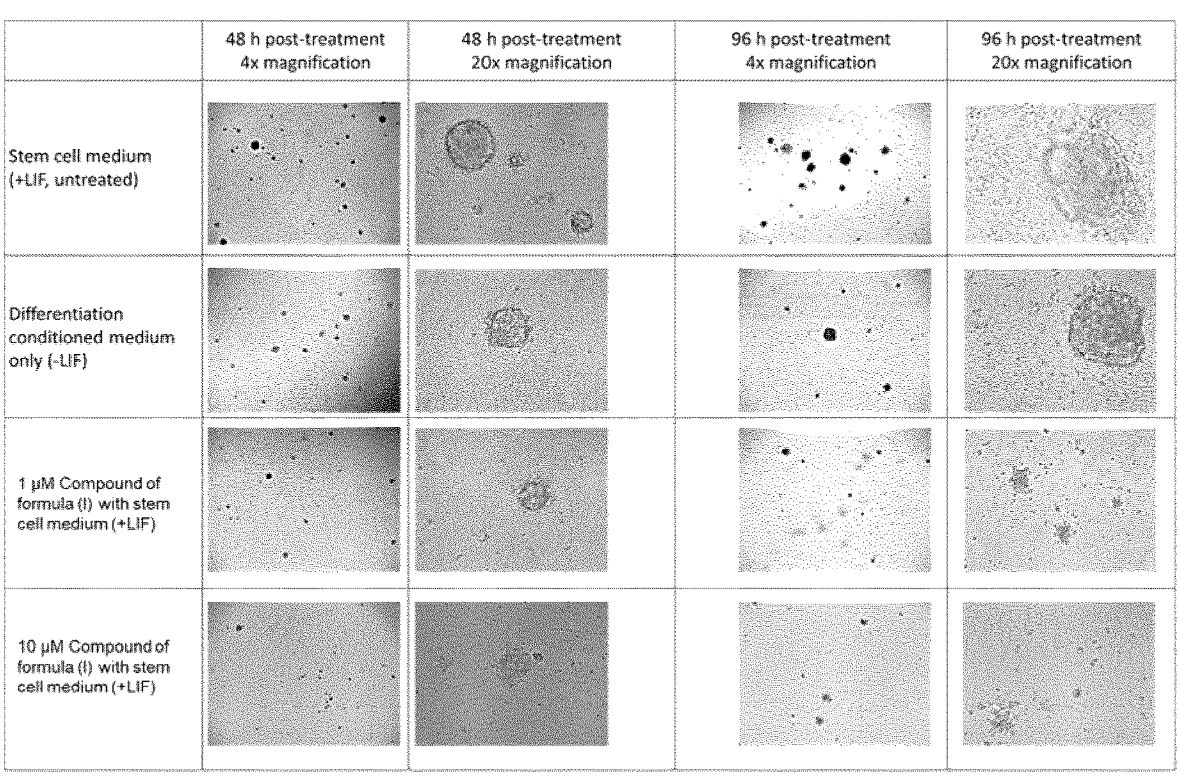
Figure 12B:
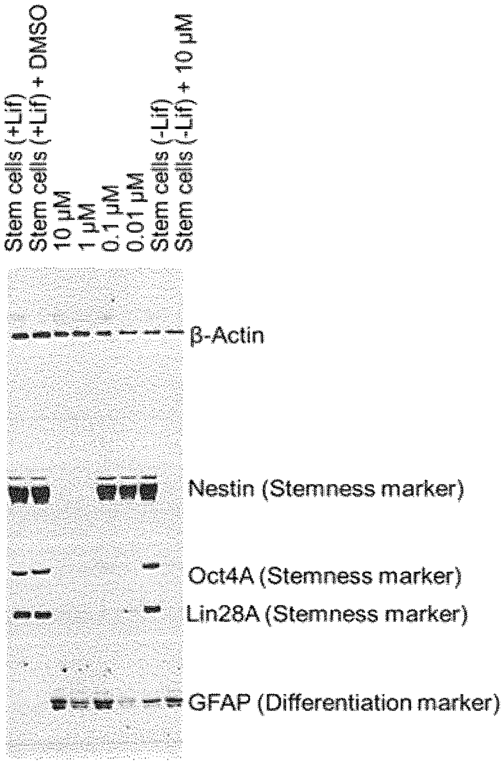

FIG. 12: Dose-dependent effect of Compound of formula (I) on the stem cell tumor spheres, in the presence of LIF—a pluripotency supplement used for maintenance of stem cell population (Panel A). As determined by western blotting, Compound of formula (I) begins to halt the expression of stemness markers (Nestin, LIN28A, Oct-4) and induces elevation of differentiation markers (GFAP), from 1 μM onwards (Panel B).

Figure 13A:
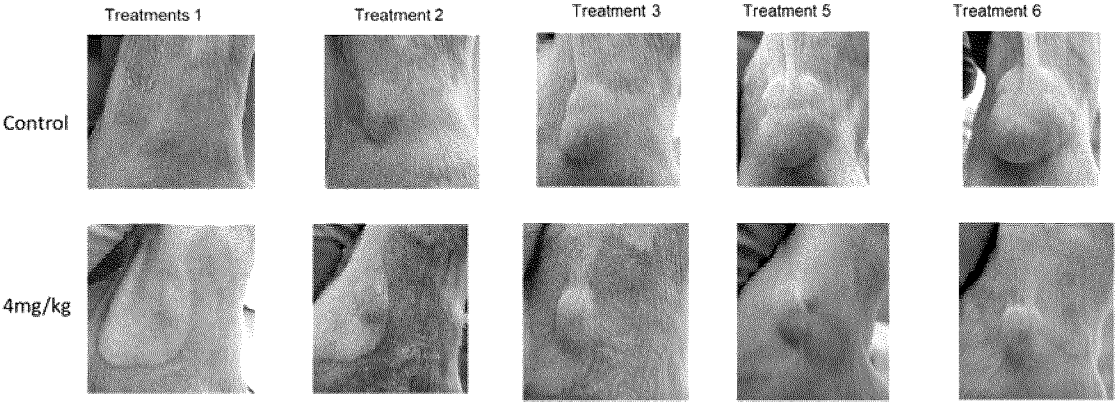
Figure 13B:
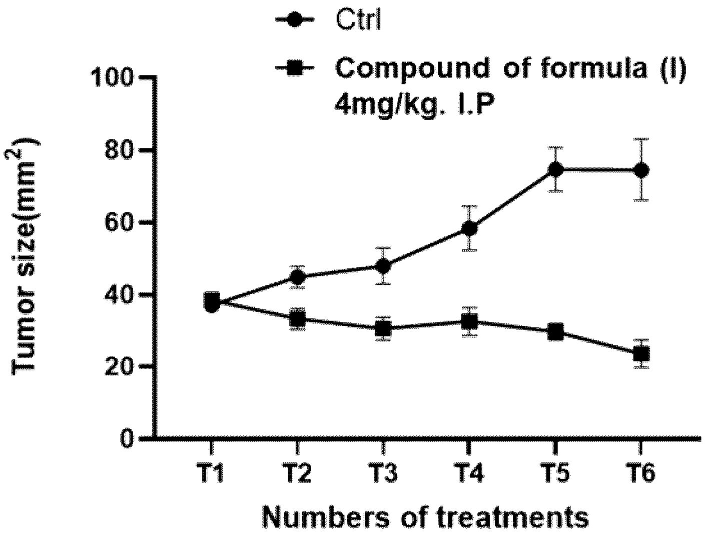

FIGS. 13A&B: Female SCID YP-MEL NCM tumor bearing mice treated with 4 mg/kg Compound of formula (I) (P1 version) intraperitoneally (I.P). (A.) Compound of formula (I) significantly reduced the growth of NCM tumors with every dose. (B) Tumor areas were measured with a Vernier caliper (prior to each treatment cycle). Animals were euthanized when the control (0.1% DMSO:PBS) treated mice reached the defined endpoint of 225 $mm^2$. Data representative of at least 5 independent experiments.

Figure 14A:
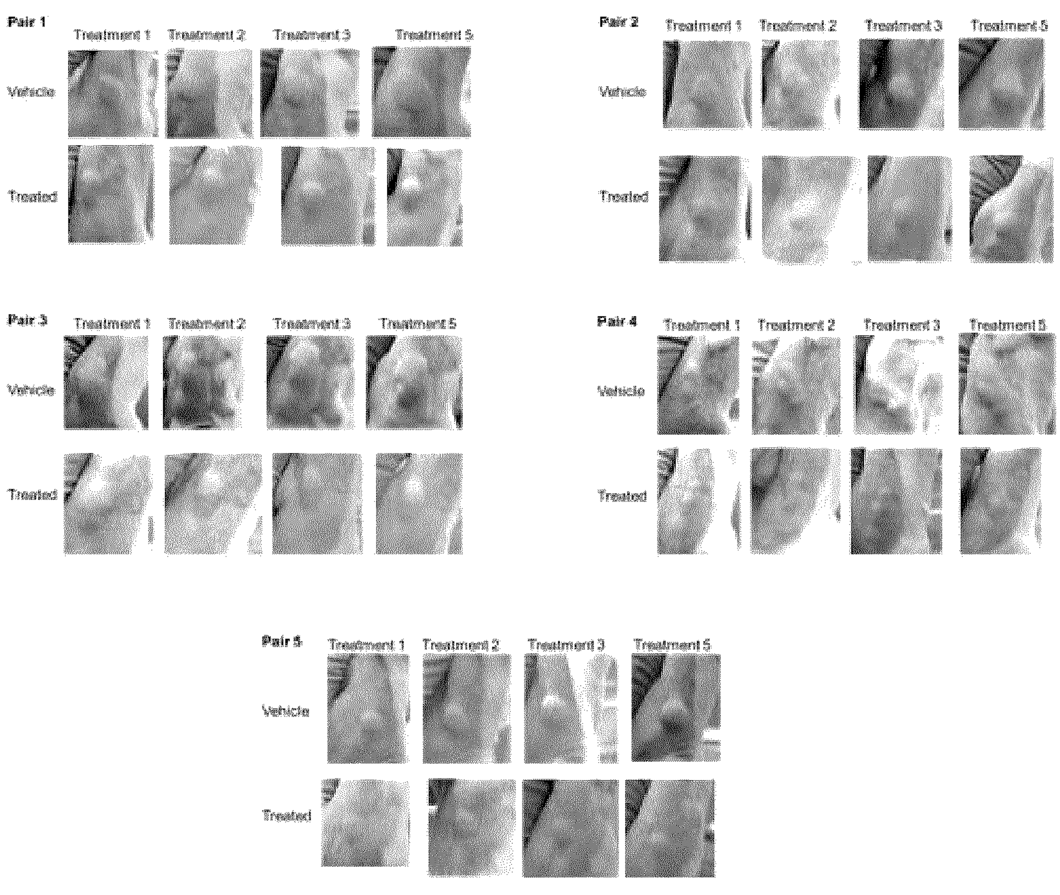
Figure 14B:
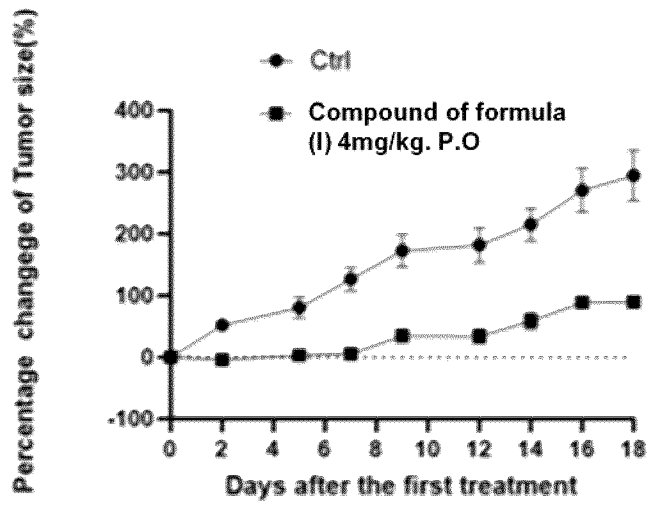
Figure 14C:
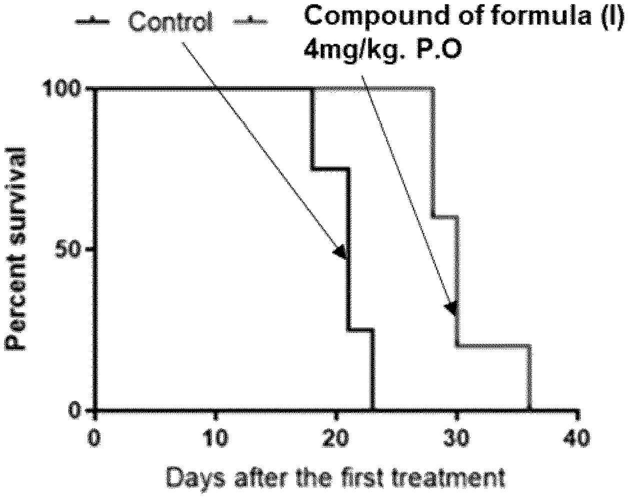
Figure 15A:
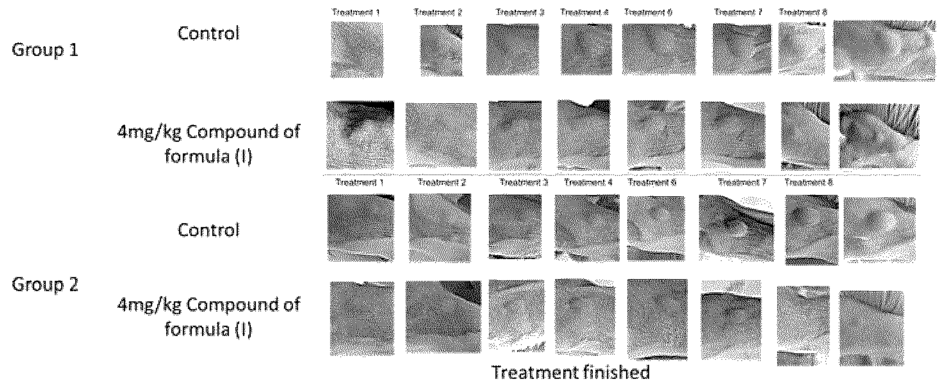
Figure 15B:
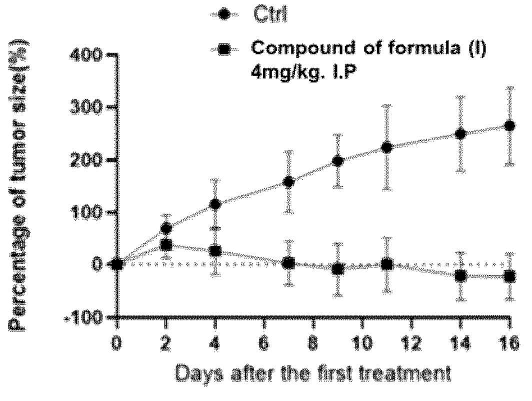
Figure 15C:
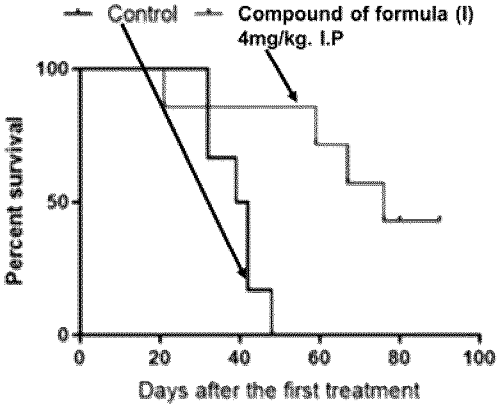
Figure 15D:
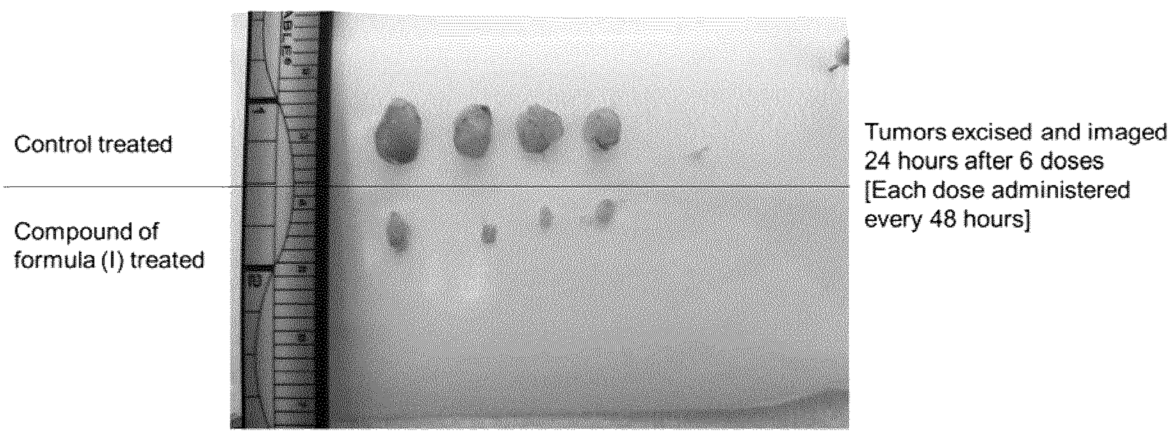

FIG. 14A-C: Male SCID NT-2 testicular tumor bearing mice treated with 4 mg/kg Compound of formula (I) (P1 version) via oral route of administration (P.O). Compound of formula (I) significantly reduced the growth of NT-2 tumors with every dose. Tumor areas were measured with a Vernier caliper (prior to each treatment cycle). Animals were euthanized when the control (0.1% DMSO:PBS) treated mice reached the defined endpoint of 225 $mm^2$. Data representative of at least 5 independent experiments. (A) shows photographs of treatment versus control. (B) is a graph depicting percentage change of tumour volume versus days after the first treatment. (C) is a graph depicting percentage survival versus days after the first treatment.

FIG. 15A-D: Male SCID NT-2 testicular tumor bearing mice treated with 4 mg/kg Compound of formula (I) (P1 version) via intraperitoneal route of administration (I.P). Compound of formula (I) significantly reduced the growth of NT-2 tumors with every dose, and at least 50% of the treated animals survived tumor-free for 120 days. Tumor areas were measured with a Vernier caliper (prior to each treatment cycle). Animals were euthanized when the control (0.1% DMSO:PBS) treated mice reached the defined endpoint of 225 $mm^2$. Data representative of at least 5 independent experiments. (A) shows photographs of treatment versus control. (B) is a graph depicting percentage of tumour size versus days after the first treatment. (C) is a graph depicting percentage survival versus days after the first treatment. (D) is a photograph showing excised tumours.

Figure 16A:
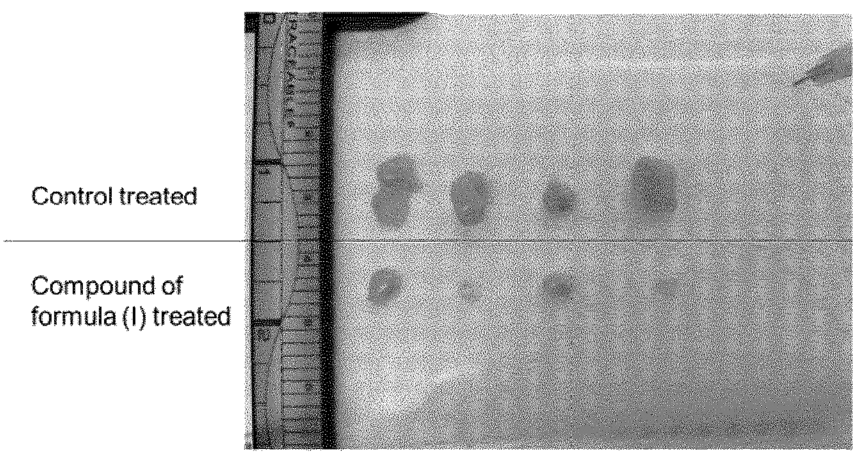
Figure 16B:
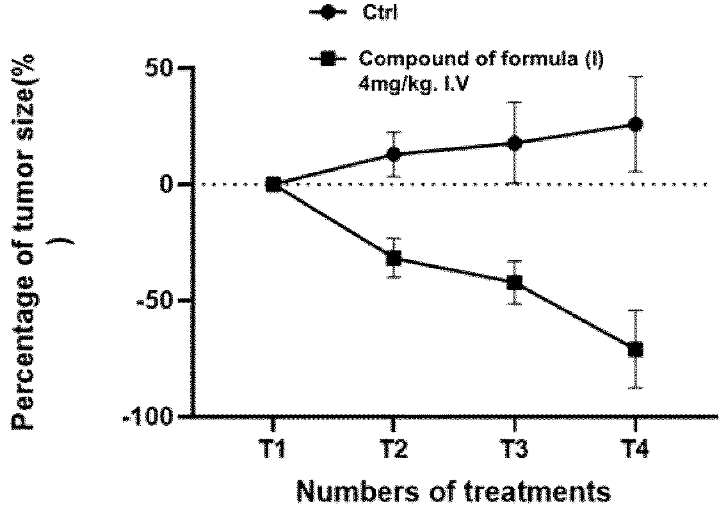

FIGS. 16A&B: Male SCID NT-2 testicular tumor bearing mice treated with 4 mg/kg Compound of formula (I) (P1 isomer) via intravenous route of administration (I.V). Compound of formula (I) significantly reduced the growth of NT-2 tumors with every dose and in some cases showed complete shrinkage with only 4 doses. Tumor areas were measured with a Vernier caliper (prior to each treatment cycle). Animals were euthanized when the control (0.1% DMSO:PBS) treated mice reached the defined endpoint of 225 $mm^2$. Data representative of at least 5 independent experiments. (A) is a photograph showing excised tumours. (B) is graph depicting percentage of tumor size versus number of treatments.

Figure 17A:
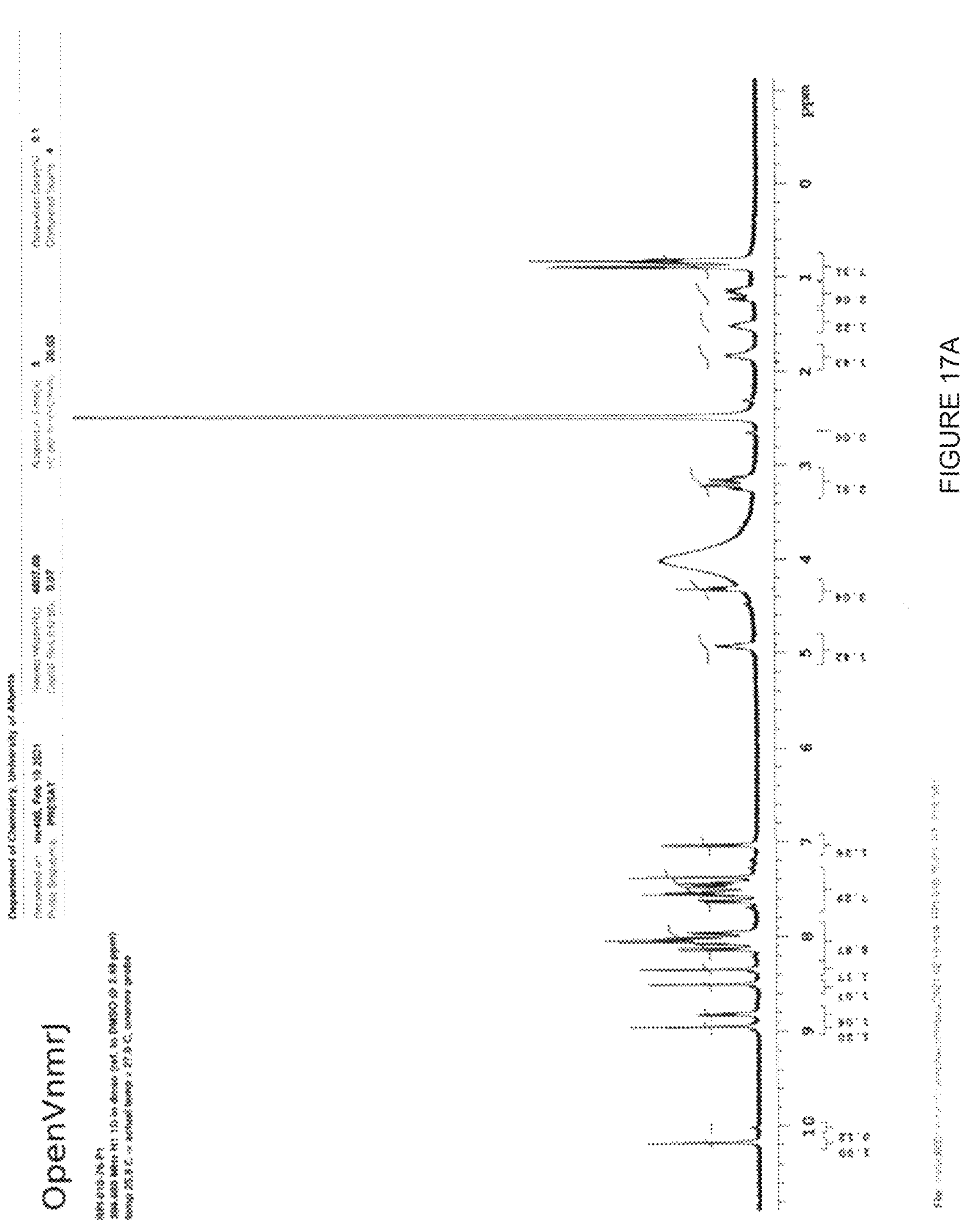
Figure 17B:
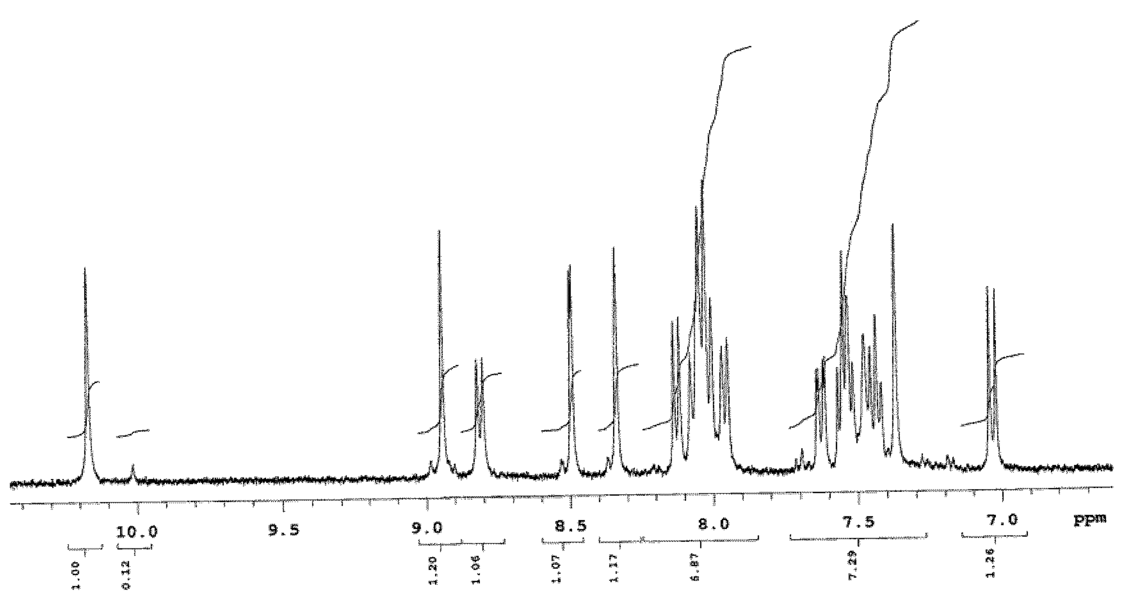
Figure 17C:
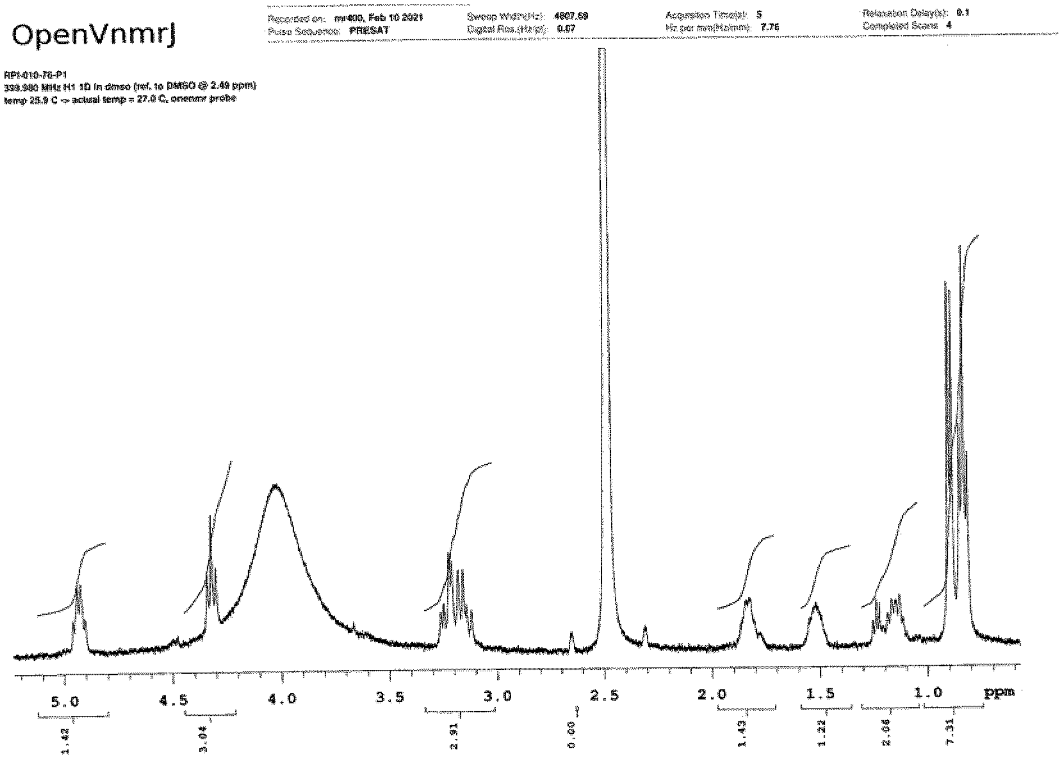
Figure 17D:
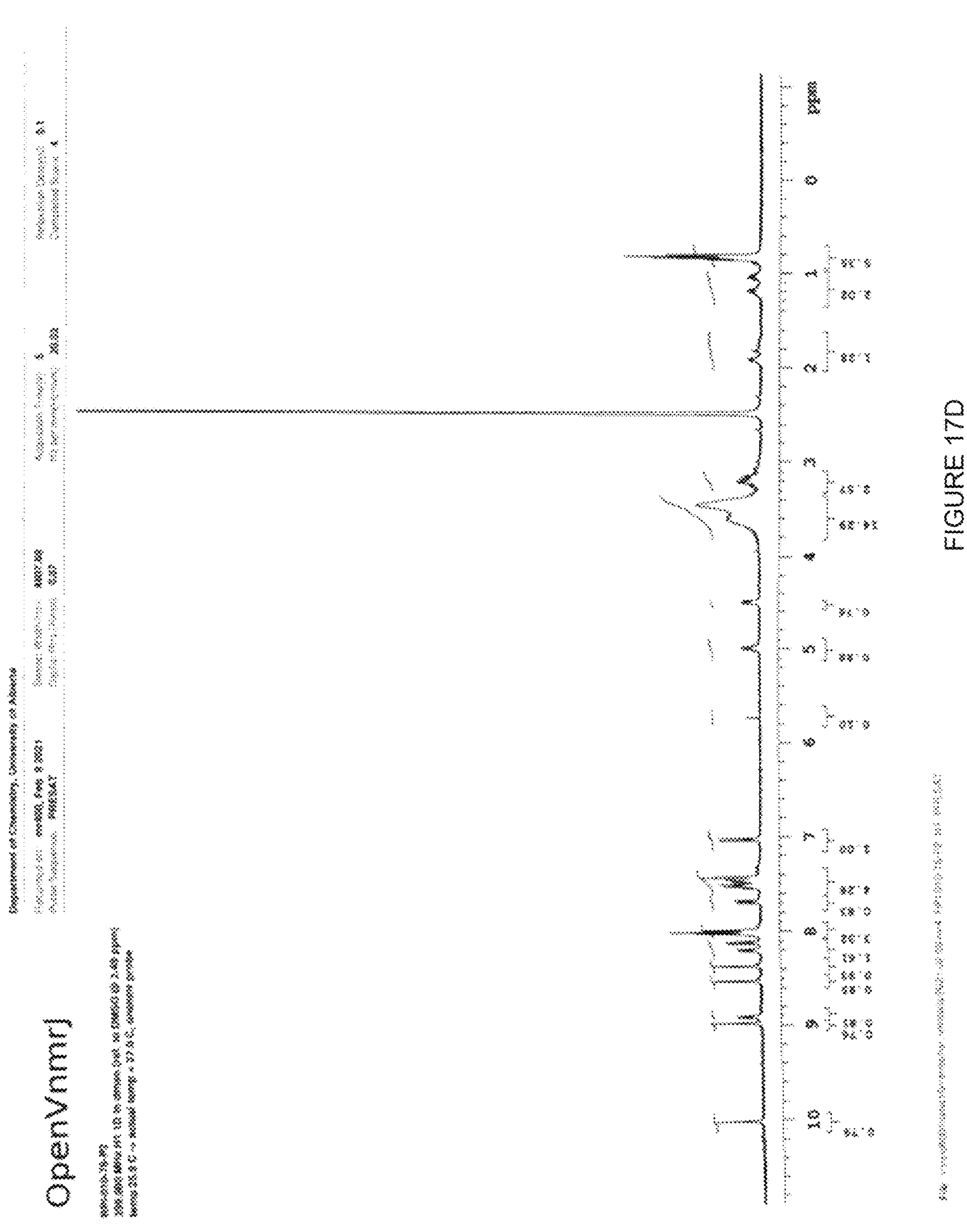
Figure 17E:
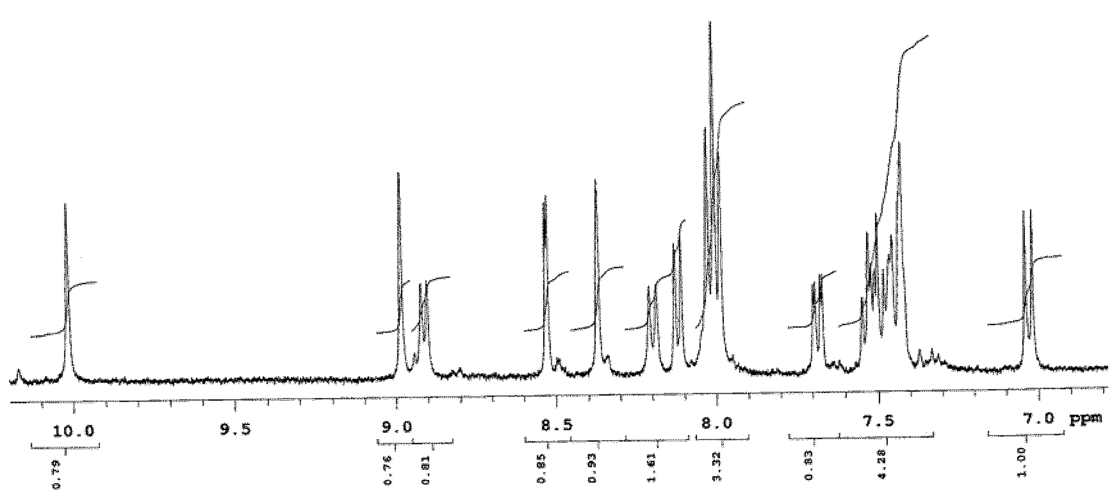
Figure 17F:
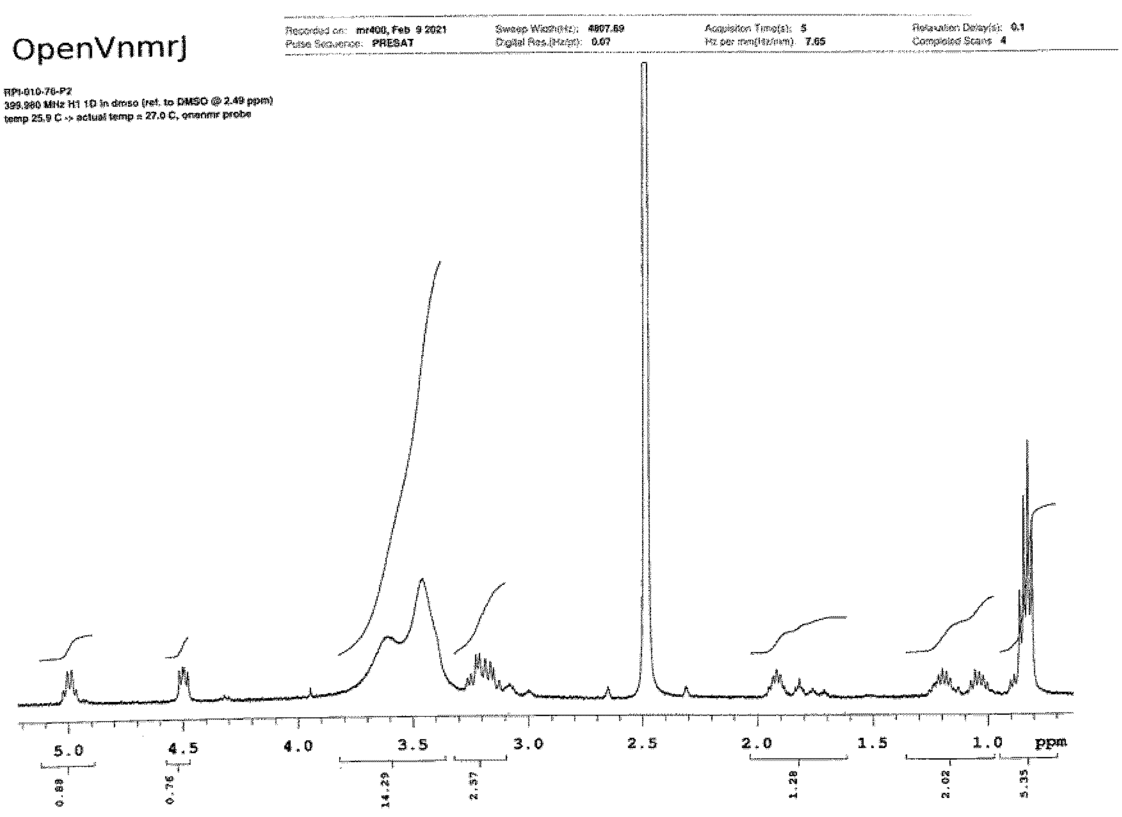
Figure 17G:
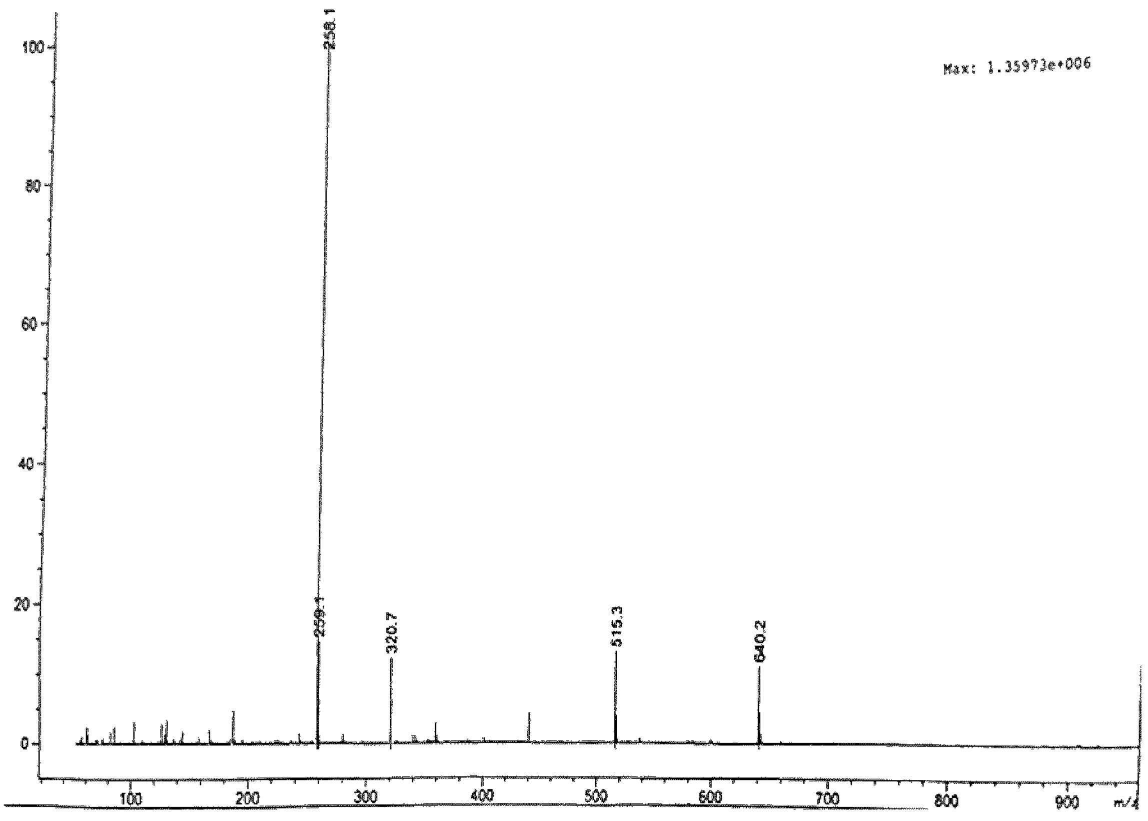

FIG. 17A-G: Analytical detection of Compound of formula (I) isomers using 1D NMR and purified P1 isomer of Compound of formula (I) detected using Liquid Chromatography Mass Spectrometry (LCMS). (17A-C) is the H1-1D NMR profile of purified P1 isomer of Compound of formula (I) dissolved in DMSO at 2.49 ppm (parts per million) at 27° C. using 400 MHz instrument. (17D-F) is the H1-1D NMR profile of purified P2 isomer of Compound of formula (I) dissolved in DMSO at 2.49 ppm (parts per million) at 27° C. using 400 MHz instrument. FIG. 17G is the mass detection of P1 Compound of formula (I) showing spectrometry ionized signal of molecular mass 640.2 $[M+H]^+$, detected using LCMS.

DETAILED DESCRIPTION

In one aspect, there is provided a compound of Formula (I):

(I)

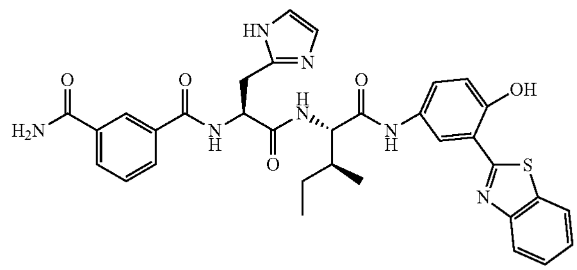

.

The compound of Formula (I) is also referred to as "Compound of formula (I)" herein.

While not wishing to be bound by theory, based on in silico structural binding assessment, the Benzamide group

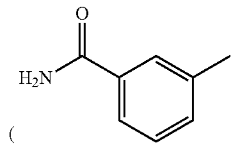

and Benzothiazole group

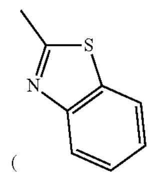

are important for interacting with the catalytic domain of LIN28A. Specifically, these moieties bind to the pre-let-7 binding region and potentially displace the GGAG miRNA fragment described in the Methodology section and FIG. 2.

In some examples, there is provided a compound of Formula I-B:

(I-B)

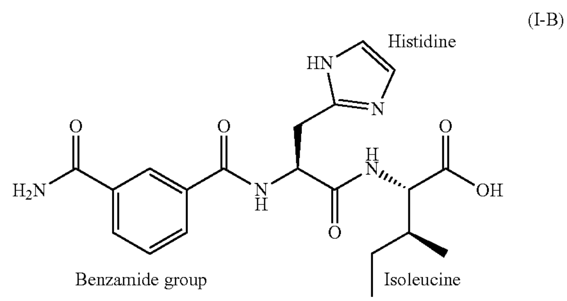 [SMILES: CC[C@H](C)[C@H](NC(=O)[C@H](Cc1ncc[nH]1)NC(=O)c1cccc(C(N)=O)c1)C(=O)O]

In this example, the "N minus 1" product (I-B) of the Compound of Formula (I) showed potential binding to both LIN28A and LIN28B with equal potency. It is the addition of Benzothiazole group that increases the binding affinity to Lin28A by 10-fold relative to Lin28B. To maintain the equipotency binding with both LIN28A and LIN28B, the Histidine and Isoleucine residues labelled, may be modified to a different basic-hydrophobic sidechain in combination with nearly equal side-chain lengths shown in I-B.

In some examples, the compounds of Formula (I) or Formula (I-B) are a tautomer, or a pharmaceutically acceptable salt, or a solvate, or a functional derivative thereof.

Compound of formula (I) underwent comprehensive purification by a slow column using normal silica gel. The two isomers were separated at the trityl protected state (compound 9 in FIG. 3). The deprotection of Trityl was achieved separately to obtain P1 and P2 isomers. The presence of these purified isomers were analytically confirmed using Nuclear Magnetic Resonance (NMR) and Mass Spectrometry.

Isomer P1-thermostable and soluble

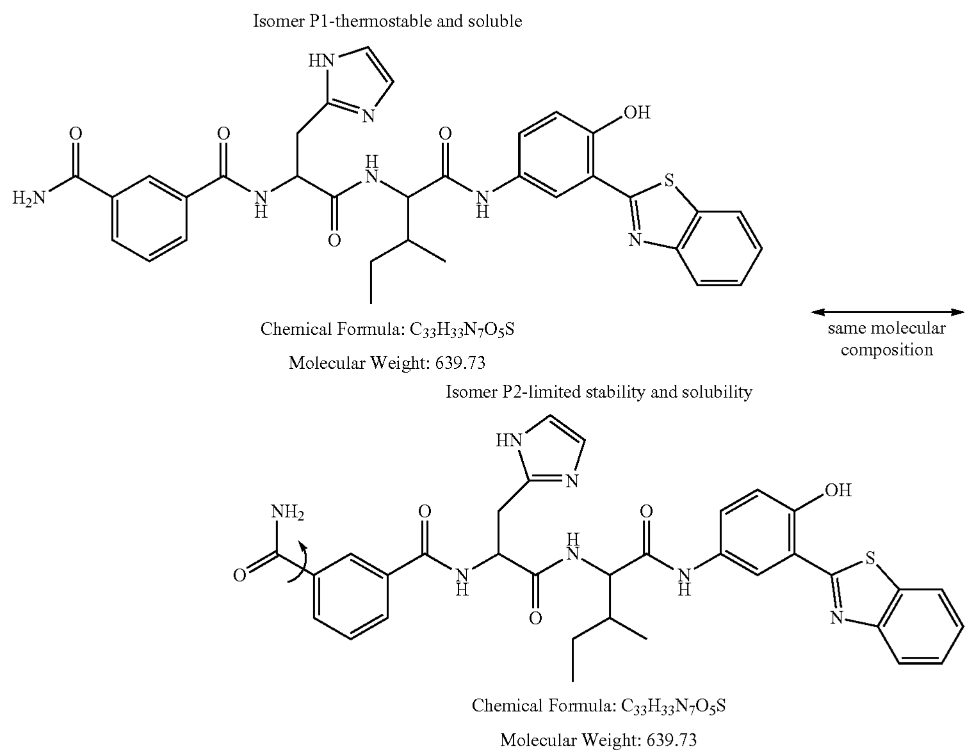

Chemical Formula: $C_{33}H_{33}N_7O_5S$

Molecular Weight: 639.73 same molecular composition

Isomer P2-limited stability and solubility

Chemical Formula: $C_{33}H_{33}N_7O_5S$

Molecular Weight: 639.73

The term "tautomer" as used herein refers to either of the two forms of a chemical compound that exhibits tautomerism, which is the ability of certain chemical compounds to exist as a mixture of two interconvertible isomers in equilibrium via proton transfer. The amide and imidic acid forms of amide compounds are examples of tautomers.

The term "functional derivative" as used herein refers to a molecule that retains a biological activity (either function or structural) that is substantially similar to that of the original compound. A functional derivative or equivalent may be a natural derivative or is prepared synthetically.

Also encompassed as prodrugs or "physiologically functional derivative".

The term "physiologically functional derivative" as used herein refers to compounds which are not pharmaceutically active themselves but which are transformed into their pharmaceutically active form in vivo, i.e. in the subject to which the compound is administered.

The term "prodrug" as used herein, refers to a derivative of a substance that, following administration, is metabolized in vivo, e.g. by hydrolysis or by processing through an enzyme, into an active metabolite.

In some examples, there is described a composition comprising a compound as described herein, and a pharmaceutically acceptable carrier, diluent, or vehicle.

Thus, in another aspect, there is provided a composition comprising a compound of Formula (I) or a compound of Formula (I-B).

In one aspect there is provided a method of treating a subject with cancer, at risk of developing cancer, or suspected of having a cancer, comprising: administering a therapeutically effective amount of a compound of Formula (I) or a compound of Formula (I-b).

In one aspect there is provided a method of treating a subject with cancer, at risk of developing cancer, or suspected of having a cancer, comprising: administering a therapeutically effective amount of a composition comprising a compound of Formula (I) or a compound of Formula (I-B).

The term "subject", as used herein, refers to an animal, and can include, for example, domesticated animals, such as cats, dogs, etc., livestock (e.g., cattle, horses, pigs, sheep, goats, etc.), laboratory animals (e.g., mouse, rabbit, rat, guinea pig, etc.), mammals, non-human mammals, primates, non-human primates, rodents, birds, reptiles, amphibians, fish, and any other animal. In a specific example, the subject is a human. In another specific example, the human is a pediatric human or an adult human.

The term "cancer", as used herein, refers to a variety of conditions caused by the abnormal, uncontrolled growth of cells. Cells capable of causing cancer, referred to as "cancer cells", possess characteristic properties such as uncontrolled proliferation, immortality, metastatic potential, rapid growth and proliferation rate, and/or certain typical morphological features. Cancer cells may be in the form of a tumour, but such cells may also exist alone within a subject, or may be a non-tumorigenic cancer cell. A cancer can be detected in any of a number of ways, including, but not limited to, detecting the presence of a tumor or tumors (e.g., by clinical or radiological means), examining cells within a tumor or from another biological sample (e.g., from a tissue biopsy), measuring blood markers indicative of cancer, and detecting a genotype indicative of a cancer. However, a negative result in one or more of the above detection methods does not necessarily indicate the absence of cancer, e.g., a patient who has exhibited a complete response to a cancer treatment may still have a cancer, as evidenced by a subsequent relapse.

The term "treatment", "treat", or "treating" as used herein, refers to obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "Treatment" can also mean prolonging survival as compared to expected survival if not receiving treatment.

The term "amelioration" or "ameliorates" as used herein refers to a decrease, reduction or elimination of a condition, disease, disorder, or phenotype, including an abnormality or symptom.

The term "symptom" of a disease or disorder is any morbid phenomenon or departure from the normal in structure, function, or sensation, experienced by a subject and indicative of disease.

A "treatment regimen" as used herein refers to a combination of dosage, frequency of administration, or duration of treatment, with or without addition of a second medication.

For example, a subject with cancer may be treated to prevent progression or alternatively a subject in remission can be treated with a compound or composition described herein to prevent recurrence.

In some examples, the cancer is Acute Myeloid Leukemia (AML), Atypical teratoid/rhabdoid tumor, Embryonal tumors with multi-layered rosettes [ETMR], Brain cancers (Pediatric and adult), Breast cancer, Cervical cancer, Sarcomas, Chronic myeloid leukemia (CML), Colon cancer, Gastric cancer, Germ cell tumors, Yolk sac tumors, gastric cancer, esophageal cancer, rectal cancers, Glioblastoma multiforme, Glioma (pediatric and adult), Liver cancer, Medulloblastoma, Multiple Myeloma, Neuroblastoma, Oral squamous cell carcinoma, Ovarian primitive germ cell tumors, Ovarian cancer (Epithelial) cancers, Pheochromocytomas, Paragangliomas, Primitive neuroectodermal tumors, Prostate cancer, Testicular germ cell tumors and Wilms tumor.

In some examples, the cancer is breast cancer (including adult breast cancer), Pediatric neurocutaneous melanosis (NCM) associated CNS tumor, pediatric atypical-teratoid rhabdoid tumor (AT/RT), adenocarcinoma (including adult adenocarcinoma), or testicular cancer.

Compounds and/or compositions comprising compounds disclosed herein may be used in the methods described herein in combination with standard treatment regimes, as would be known to the skilled worker.

A compound or composition may be administered alone or in combination with other treatments, either simultaneously or sequentially, dependent upon the condition to be treated.

Existing treatment of certain cancers are known.

In some examples, combination therapies may be used in one or more for the following cancers: Acute Myeloid Leukemia (AML), Atypical teratoid/rhabdoid tumor, Embryonal tumors with multi-layered rosettes [ETMR], Brain cancers (Pediatric and adult), Breast cancer, Cervical cancer, Sarcomas, Chronic myeloid leukemia (CML), Colon cancer, Gastric cancer, esophageal cancer, rectal cancers, Germ cell tumors, Yolk sac tumors, Glioblastoma multiforme, Glioma (pediatric and adult), Liver cancer, Medulloblastoma, Multiple Myeloma, Neuroblastoma, Oral squamous cell carcinoma, Ovarian primitive germ cell tumors, Ovarian cancer (Epithelial) cancers, Pheochromocytomas, Paragangliomas, Primitive neuroectodermal tumors, Prostate cancer, Testicular germ cell tumors and Wilms tumor.

In some examples, combination therapies may be used in one or more for the following cancers: breast cancer (including adult breast cancer), Pediatric neurocutaneous melanosis (NCM) associated CNS tumor, pediatric atypical-teratoid rhabdoid tumor (AT/RT), adenocarcinoma (including adult adenocarcinoma), or testicular cancer.

In one example, drugs (and combinations of drug) approved by the US FDA may be found at https://www.cancer.gov/about-cancer/treatment/drugs/cancer-type.

The therapeutic formulation herein may also contain more than one active compound as necessary for the particular indication being treated, typically those with complementary activities that do not adversely affect each other. Such molecules are suitably present in combination in amounts that are effective for the purpose intended.

Accordingly, in one example, the compounds and compositions described herein may be used in combination with one or more of the drugs and/or drug combination that are know, for example those found at //www.cancer.gov/about-cancer/treatment/drugs/cancer-type.

In another examples, the compounds and compositions described herein may be used in combination with one or more of the drugs and/or drug combination described herein, and as follows.

Drugs Approved for Acute Myeloid Leukemia (AML)

Arsenic Trioxide, Azacitidine, Cerubidine (Daunorubicin Hydrochloride), Cyclophosphamidel, Cytarabine, Daunorubicin Hydrochloride, Daunorubicin Hydrochloride and Cytarabine Liposome, Daurismo (Glasdegib Maleate), Dexamethasone, Doxorubicin Hydrochloride, Enasidenib Mesylate, Gemtuzumab Ozogamicin, Gilteritinib Fumarate, Glasdegib Maleate, Idamycin PFS (Idarubicin Hydrochloride), Idarubicin Hydrochloride, Idhifa (Enasidenib Mesylate), Ivosidenib, Midostaurin, Mitoxantrone Hydrochloride, Mylotarg (Gemtuzumab Ozogamicin), Onureg (Azacitidine), Prednisone, Rubidomycin (Daunorubicin Hydrochloride), Rydapt (Midostaurin), Tabloid (Thioguanine), Thioguanine, Tibsovo (Ivosidenib), Trisenox (Arsenic Trioxide), Venclexta (Venetoclax), Venetoclax, Vincristine Sulfate, Vyxeos (Daunorubicin Hydrochloride and Cytarabine Liposome), Xospata (Gilteritinib Fumarate).

Drug Combinations Used in Acute Myeloid Leukemia (AML), ADE.

Drugs Approved for Acute Myeloid Leukemia (AML)

Arsenic Trioxide, Azacitidine, Cerubidine (Daunorubicin Hydrochloride), Cyclophosphamidel, Cytarabine, Daunorubicin Hydrochloride, Daunorubicin Hydrochloride and Cytarabine Liposome, Daurismo (Glasdegib Maleate), Dexamethasone, Doxorubicin Hydrochloride, Enasidenib Mesylate, Gemtuzumab Ozogamicin, Gilteritinib Fumarate, Glasdegib Maleate, Idamycin PFS (Idarubicin Hydrochloride), Idarubicin Hydrochloride, Idhifa (Enasidenib Mesylate), Ivosidenib, Midostaurin, Mitoxantrone Hydrochloride, Mylotarg (Gemtuzumab Ozogamicin), Onureg (Azacitidine), Prednisone, Rubidomycin (Daunorubicin Hydrochloride), Rydapt (Midostaurin), Tabloid (Thioguanine), Thioguanine, Tibsovo (Ivosidenib), Trisenox (Arsenic Trioxide), Venclexta (Venetoclax), Venetoclax, Vincristine Sulfate, Vyxeos (Daunorubicin Hydrochloride and Cytarabine Liposome), Xospata (Gilteritinib Fumarate), Drug Combinations Used in Acute Myeloid Leukemia (AML), ADE.

Drugs Approved for Brain Tumours

Afinitor (Everolimus), Afinitor Disperz (Everolimus), Avastin (Bevacizumab), Bevacizumab, BiCNU (Carmustine), Carmustine, Carmustine Implant, Everolimus, Gliadel Wafer (Carmustine Implant), Lomustine, Mvasi (Bevacizumab), Temodar (Temozolomide), Temozolomide, Zirabev (Bevacizumab), PCV.

Drugs Approved to Prevent Breast Cancer

Evista (Raloxifene Hydrochloride), Raloxifene Hydrochloride, Soltamox (Tamoxifen Citrate), Tamoxifen Citrate.

Drugs Approved to Treat Breast Cancer

Abemaciclib, Abraxane (Paclitaxel Albumin-stabilized Nanoparticle Formulation), Ado-Trastuzumab Emtansine, Afinitor (Everolimus), Afinitor Disperz (Everolimus), Alpelisib, Anastrozole, Aredia (Pamidronate Disodium), Arimidex (Anastrozole), Aromasin (Exemestane), Atezolizumab, Capecitabine, Cyclophosphamide, Docetaxel, Doxorubicin Hydrochloride, Ellence (Epirubicin Hydrochloride), Enhertu (Fam-Trastuzumab Deruxtecan-nxki), Epirubicin Hydrochloride, Eribulin Mesylate, Everolimus, Exemestane, 5-FU (Fluorouracil Injection), Fam-Trastuzumab Deruxtecan-nxki, Fareston (Toremifene), Faslodex (Fulvestrant), Femara (Letrozole), Fluorouracil Injection, Fulvestrant, Gemcitabine Hydrochloride, Gemzar (Gemcitabine Hydrochloride), Goserelin Acetate, Halaven (Eribulin Mesylate), Herceptin Hylecta (Trastuzumab and Hyaluronidase-oysk), Herceptin (Trastuzumab), Ibrance (Palbociclib), Infugem (Gemcitabine Hydrochloride), Ixabepilone, Ixempra (Ixabepilone), Kadcyla (Ado-Trastuzumab Emtansine), Keytruda (Pembrolizumab), Kisqali (Ribociclib), Lapatinib Ditosylate, Letrozole, Lynparza (Olaparib), Margenza (Margetuximab-cmkb), Margetuximab-cmkb, Megestrol Acetate, Methotrexate Sodium, Neratinib Maleate, Nerlynx (Neratinib Maleate), Olaparib, Paclitaxel, Paclitaxel Albumin-stabilized Nanoparticle Formulation, Palbociclib, Pamidronate Disodium, Pembrolizumab, Perjeta (Pertuzumab), Pertuzumab, Pertuzumab, Trastuzumab, and Hyaluronidase-zzxf, Phesgo (Pertuzumab, Trastuzumab, and Hyaluronidase-zzxf), Piqray (Alpelisib), Ribociclib, Sacituzumab Govitecan-hziy, Soltamox (Tamoxifen Citrate), Talazoparib Tosylate, Talzenna (Talazoparib Tosylate), Tamoxifen Citrate, Taxotere (Docetaxel), Tecentriq (Atezolizumab), Tepadina (Thiotepa), Thiotepa, Toremifene, Trastuzumab, Trastuzumab and Hyaluronidase-oysk, Trexall (Methotrexate Sodium), Trodelvy (Sacituzumab Govitecan-hziy), Tucatinib, Tukysa (Tucatinib), Tykerb (Lapatinib Ditosylate), Verzenio (Abemaciclib), Vinblastine Sulfate, Xeloda (Capecitabine), Zoladex (Goserelin Acetate), AC, AC-T, CAF, CMF, FEC, TAC.

Drugs Approved to Prevent Cervical Cancer

Cervarix (Recombinant HPV Bivalent Vaccine), Gardasil (Recombinant HPV Quadrivalent Vaccine), Gardasil 9 (Recombinant HPV Nonavalent Vaccine), Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine.

Drugs Approved to Treat Cervical Cancer

Avastin (Bevacizumab), Bevacizumab, Bleomycin Sulfate, Hycamtin (Topotecan Hydrochloride), Keytruda (Pembrolizumab), Mvasi (Bevacizumab), Pembrolizumab, Topotecan Hydrochloride, Zirabev (Bevacizumab). Gemcitabine-Cisplatin.

Drugs Approved for Kaposi Sarcoma

Doxil (Doxorubicin Hydrochloride Liposome), Doxorubicin Hydrochloride Liposome, Intron A (Recombinant Interferon Alfa-2b), Paclitaxel, Pomalidomide, Pomalyst (Pomalidomide), Recombinant Interferon Alfa-2b, Vinblastine Sulfate.

Drugs Approved for Chronic Myelogenous Leukemia (CML)

Bosulif (Bosutinib), Bosutinib, Busulfan, Busulfex (Busulfan), Cyclophosphamide, Cytarabine, Dasatinib, Dexamethasone, Gleevec (Imatinib Mesylate), Hydrea (Hydroxyurea), Hydroxyurea, Iclusig (Ponatinib Hydrochloride), Imatinib Mesylate, Myleran (Busulfan), Nilotinib, Omacetaxine Mepesuccinate, Ponatinib Hydrochloride, Sprycel (Dasatinib), Synribo (Omacetaxine Mepesuccinate), Tasigna (Nilotinib).

Drugs Approved for Colon Cancer

Avastin (Bevacizumab), Bevacizumab, Camptosar (Irinotecan Hydrochloride), Capecitabine, Cetuximab, Cyramza (Ramucirumab), Eloxatin (Oxaliplatin), Erbitux (Cetuximab), 5-FU (Fluorouracil Injection), Fluorouracil Injection, Ipilimumab, Irinotecan Hydrochloride, Keytruda (Pembrolizumab), Leucovorin Calcium, Lonsurf (Trifluridine and Tipiracil Hydrochloride), Mvasi (Bevacizumab), Nivolumab, Opdivo (Nivolumab), Oxaliplatin, Panitumumab, Pembrolizumab, Ramucirumab, Regorafenib, Stivarga (Regorafenib), Trifluridine and Tipiracil Hydrochloride, Vectibix (Panitumumab), Xeloda (Capecitabine), Yervoy (Ipilimumab), Zaltrap (Ziv-Aflibercept), Zirabev (Bevacizumab), Ziv-Aflibercept, Drug Combinations Used in Colon Cancer, CAPOX, FOLFIRI, FOLFIRI-BEVACIZUMAB, FOLFIRI-CETUXIMAB, FOLFOX, FU-LV, XELIRI, XELOX.

Drugs Approved for Rectal Cancer

Avastin (Bevacizumab), Bevacizumab, Camptosar (Irinotecan Hydrochloride), Capecitabine, Cetuximab, Cyramza (Ramucirumab), Eloxatin (Oxaliplatin), Erbitux (Cetuximab), 5-FU (Fluorouracil Injection), Fluorouracil Injection, Ipilimumab, Irinotecan Hydrochloride, Keytruda (Pembrolizumab), Leucovorin Calcium, Lonsurf (Trifluridine and Tipiracil Hydrochloride), Mvasi (Bevacizumab), Nivolumab, Opdivo (Nivolumab), Oxaliplatin, Panitumumab, Pembrolizumab, Ramucirumab, Regorafenib, Stivarga (Regorafenib), Trifluridine and Tipiracil Hydrochloride, Vectibix (Panitumumab), Xeloda (Capecitabine), Yervoy (Ipilimumab), Zaltrap (Ziv-Aflibercept), Zirabev (Bevacizumab), Ziv-Aflibercept, CAPOX, FOLFIRI.

Drugs Approved for Stomach (Gastric) Cancer

Cyramza (Ramucirumab), Docetaxel, Doxorubicin Hydrochloride, 5-FU (Fluorouracil Injection), Fluorouracil Injection, Herceptin (Trastuzumab), Keytruda (Pembrolizumab), Lonsurf (Trifluridine and Tipiracil Hydrochloride), Mitomycin, Pembrolizumab, Ramucirumab, Taxotere (Docetaxel), Trastuzumab, Trifluridine and Tipiracil Hydrochloride.

Drug Combinations Used in Stomach (Gastric) Cancer

FU-LV, TPF, XELIRI

Drugs Approved for Esophageal Cancer

Keytruda (Pembrolizumab), Nivolumab, Opdivo (Nivolumab), Pembrolizumab, Drug Combinations Used in Esophageal Cancer, FU-LV, XELIRI.

Drugs Approved for Gastroesophageal Junction Cancer

Cyramza (Ramucirumab), Docetaxel, Herceptin (Trastuzumab), Keytruda (Pembrolizumab), Lonsurf (Trifluridine and Tipiracil Hydrochloride), Pembrolizumab, Ramucirumab, Taxotere (Docetaxel), Trastuzumab, Trifluridine and Tipiracil Hydrochloride.

Drugs Approved for Liver Cancer

Atezolizumab, Avastin (Bevacizumab), Bevacizumab, Cabometyx (Cabozantinib-S-Malate), Cabozantinib-S-Malate, Cyramza (Ramucirumab), Keytruda (Pembrolizumab), Lenvatinib Mesylate, Lenvima (Lenvatinib Mesylate), Nexavar (Sorafenib Tosylate), Nivolumab, Opdivo (Nivolumab), Pemazyre (Pemigatinib), Pembrolizumab, Pemigatinib, Ramucirumab, Regorafenib, Sorafenib Tosylate, Stivarga (Regorafenib),Tecentriq (Atezolizumab).

Drugs Approved for Multiple Myeloma and Other Plasma Cell Neoplasms

Alkeran for Injection (Melphalan Hydrochloride), Alkeran Tablets (Melphalan), Aredia (Pamidronate Disodium), Belantamab Mafodotin-blmf, BiCNU (Carmustine), Blenrep (Belantamab Mafodotin-blmf), Bortezomib, Carfilzomib, Carmustine, Cyclophosphamide, Daratumumab, Daratumumab and Hyaluronidase-fihj, Darzalex (Daratumumab), Darzalex Faspro (Daratumumab and Hyaluronidase-fihj), Doxil (Doxorubicin Hydrochloride Liposome), Doxorubicin Hydrochloride Liposome, Elotuzumab, Empliciti (Elotuzumab), Evomela (Melphalan Hydrochloride), Farydak (Panobinostat Lactate), lsatuximab-irfc, Ixazomib Citrate, Kyprolis (Carfilzomib), Lenalidomide, Melphalan, Melphalan Hydrochloride, Mozobil (Plerixafor), Ninlaro (Ixazomib Citrate), Pamidronate Disodium, Panobinostat Lactate, Plerixafor, Pomalidomide, Pomalyst (Pomalidomide), Revlimid (Lenalidomide), Sarclisa (Isatuximab-irfc), Selinexor, Thalidomide, Thalomid (Thalidomide), Velcade (Bortezomib), Xpovio (Selinexor), Zoledronic Acid, Zometa (Zoledronic Acid), Drug Combinations Used in Multiple Myeloma and Other Plasma Cell Neoplasms

PAD.

Drugs Approved for Neuroblastoma

Cyclophosphamide, Danyelza (Naxitamab-gqgk), Dinutuximab, Doxorubicin Hydrochloride, Naxitamab-gqgk, Unituxin (Dinutuximab), Vincristine Sulfate.

Drug Combinations Used in Neuroblastoma

BuMel, CEM.

Drugs Approved for Multiple Myeloma and Other Plasma Cell Neoplasms

Alkeran for Injection (Melphalan Hydrochloride), Alkeran Tablets (Melphalan), Aredia (Pamidronate Disodium), Belantamab Mafodotin-blmf, BiCNU (Carmustine), Blenrep (Belantamab Mafodotin-blmf), Bortezomib, Carfilzomib, Carmustine, Cyclophosphamide, Daratumumab, Daratumumab and Hyaluronidase-fihj, Darzalex (Daratumumab), Darzalex Faspro (Daratumumab and Hyaluronidase-fihj), Doxil (Doxorubicin Hydrochloride Liposome), Doxorubicin Hydrochloride Liposome, Elotuzumab, Empliciti (Elotuzumab), Evomela (Melphalan Hydrochloride), Farydak (Panobinostat Lactate), lsatuximab-irfc, Ixazomib Citrate, Kyprolis (Carfilzomib), Lenalidomide, Melphalan, Melphalan Hydrochloride, Mozobil (Plerixafor), Ninlaro (Ixazomib Citrate), Pamidronate Disodium, Panobinostat Lactate, Plerixafor, Pomalidomide, Pomalyst (Pomalidomide), Revlimid (Lenalidomide), Sarclisa (Isatuximab-irfc), Selinexor, Thalidomide, Thalomid (Thalidomide), Velcade (Bortezomib), Xpovio (Selinexor), Zoledronic Acid, Zometa (Zoledronic Acid), Drug Combinations Used in Multiple Myeloma and Other Plasma Cell Neoplasms

PAD.

Drugs Approved for Cutaneous Squamous Cell Carcinoma

Cemiplimab-rwlc, Keytruda (Pembrolizumab), Libtayo (Cemiplimab-rwlc), Pembrolizumab.

Drugs Approved for Prostate Cancer

Abiraterone Acetate, Apalutamide, Bicalutamide, Cabazitaxel, Casodex (Bicalutamide), Darolutamide, Degarelix, Docetaxel, Eligard (Leuprolide Acetate), Enzalutamide, Erleada (Apalutamide), Firmagon (Degarelix), Flutamide, Goserelin Acetate, Jevtana (Cabazitaxel), Leuprolide Acetate, Lupron Depot (Leuprolide Acetate), Lynparza (Olaparib), Mitoxantrone Hydrochloride, Nilandron (Nilutamide), Nilutamide, Nubeqa (Darolutamide), Olaparib, Orgovyx (Relugolix), Provenge (Sipuleucel-T), Radium 223 Dichloride, Relugolix, Rubraca (Rucaparib Camsylate), Rucaparib Camsylate, Sipuleucel-T, Taxotere (Docetaxel), Xofigo (Radium 223 Dichloride), Xtandi (Enzalutamide), Yonsa (Abiraterone Acetate), Zoladex (Goserelin Acetate), Zytiga (Abiraterone Acetate).

Drugs Approved for Testicular Cancer

Bleomycin Sulfate, Cisplatin, Cosmegen (Dactinomycin), Dactinomycin, Etopophos (Etoposide Phosphate), Etoposide, Etoposide Phosphate, Ifex (Ifosfamide), Ifosfamide, Vinblastine Sulfate.

Drug Combinations Used in Testicular Cancer

BEP, JEB, PEB, VeIP, VIP.

Drugs Approved for Wilms Tumor and Other Childhood Kidney Cancers

Cosmegen (Dactinomycin), Dactinomycin, Doxorubicin Hydrochloride, Vincristine Sulfate.

In one example, it is shown that a dose dependent reduction of sternness markers and elevation of differentiation markers in the stem cell population, mediated by the compounds and compositions as described herein, for example the compound of Formula (I) (Compound of formula (I)).

In some examples, the compounds and compositions described herein, for example the compound of Formula (I) (Compound of formula (I)), may be used to target cancers, where cancer cells have LIN28A, LIN28B and associated let-7 repression and/or mutations.

As used here in "mutation" refers to molecular changes including single nucleotide polymorphisms (SNPs) which is caused by a single nucleotide change in the gene, insertion/deletions in the DNA sequence, or a mutation in the gene. Such mutations that alter the eventual levels of LIN28A and LIN28B and let7 may be determined by molecular analyses that specifically detect the alterations indicated. Techniques commonly used for this include DNA and RNA sequencing and polymerase chain reaction (PCR). A commonly used method is to amplify the sequence of LIN28A and LIN28B sequence in a tumor and the polymorphisms and mutations in the sequence can then be detected by DNA sequencing or by a method called single strand conformation polymorphism analysis. In addition, an increase in LIN28A and LIN28B levels may be detected by western blot analysis and/or immunohistochemistry (IHC) on tumor tissues.

Accordingly, in some examples, a mutation in a gene refers to a polymorphism, a deletion, an insertion or substitution of one or more nucleotides, relative to the wild-type nucleotide sequence. In some examples there is more than one mutation.

Normally, mature let-7 functions like a tumor suppressor. Therefore, a reduction in let-7 leads to the initiation and progression of cancer. This occurs when there is an increase in the expression and/or of LIN28 because LIN28 binds to the immature form of let-7 and prevents its maturation. Molecular changes such as mutations and SNPs that occur in the LIN28 gene leads to the production of increased amounts or more active proteins in the cells leading to lesser levels of mature let7 and more oncogenesis. Hence, the blocking of the interaction between the abnormal LIN28 and immature let-7 by the compounds and compositions as described here, for example the compound of Formula (1) (Compound of formula (I)) lends the anticancer properties of the agent.

In some example, the compounds and compositions as described herein, for example the compound of Formula (1) (Compound of formula (I)), may be used to treat a cancer which cancer cells overexpress LIN28A, LIN28B and have associated repression of let-7 miRNA.

In some examples, overexpression refers to over expression of LIN28A protein and/or LIN28B protein.

In some examples, overexpression refers to over expression of the LIN28A gene and/or LIN28B gene.

In some examples, overexpression of LIN28A and LIN28B proteins may be caused by the genomic alterations resulting from SNPs and mutations and insertion/deletions.

In some examples, the compounds and compositions as described herein, for example the compound of formula (I) (Compound of formula (I)) may be used to treat a cancer which cancer cells comprise gene SNPs, mutations, amplification and/or increased protein expression of LIN28A and LIN28B.

In some examples, a mutation is a change in the DNA sequence of LIN28A and LIN28B genes that leads to an increased expression of the LIN28 protein, will be targeted. A number of SNPs in the LIN28 gene have been shown to be associated with various cancers. These include rs3811464 G>A, rs3811463 T>C, rs34787247 G>A and rs11247957 G>A. Overall, we found that rs3811463 T>C and rs34787247 G>A [37].

In some examples, the compounds and compositions described herein, for example a compound of Formula (I) (Compound of formula (I)), may be used to treat tumors with a cross-reactive and therapeutically beneficial target in cancer patients. These include, but are not limited to, Insulin-like growth factor 2 (Igf2), OCT4, H2a, Cyclin A, Cyclin B, CDK4 K-RAS, C-MYC and HMGA2, morphogenetic proteins 4 (BMP4). LIN28A and LIN28 mediated changes in these proteins have been shown to increase cancer growth and survival [38].

In some examples, the compounds and compositions described herein, for example a compound of Formula (I) (Compound of formula (I)), may be used to kill cancer stem cells. Within the tumor microenvironment, a small number of cells exist with the ability for self-renewal and propagation. These cells are called tumor initiating cells or cancer stem cells (CSCs). Such cells have been shown to play a significant role in cancer growth, survival and the generation of treatment resistance. LIN28A and LIN28B have been shown to regulate the formation of CSCs by increasing the levels of let-7. Studies have shown that the increased expression of LIN28 in breast cancer correlates with over-expression of HER2 in breast cancer [39]. Consequently, the inhibition of LIN28 by the compounds and compositions as described herein, for example a compound of Formula (I) (Compound of formula (I)), are expected to result in cancer stem cell elimination and increased anti-tumor effects.

In some examples, the compounds and compositions described herein, for example a compound of Formula (I) (Compound of formula (I)), may be used to treat cancers that are resistant to chemotherapeutics. The compounds and compositions that target LIN28//et-7 axis will increase capability to eradicate CSCs than conventional chemotherapeutics. The inhibitory effect of the compound Formula (I) (Compound of formula (I)), on CSCs through the inhibition of LIN28A and LIN28B and the subsequent increase in let-7 levels may lead to increased sensitivity chemotherapeutic agents and may reverse previously seen drug resistance [40].

In some examples, the compounds and compositions described herein, for example a compound of Formula (I) (Compound of formula (I)), may be used in combination with therapeutic radiation treatments, for the treatment of cancer in a subject. Tumors that contain rapidly growing malignant cells are typically sensitive to radiation. These include embryonal tumors, sarcomas, malignant lymphomas, head and neck cancers, breast cancer, colon and lung cancer as well as other hematological malignancies. Treatment modalities include external beam radiation, brachytherapy (internal radiation) and systemic radiation.

In some examples, the compounds and compositions described herein, for example a compound of Formula (I) (Compound of formula (I)), may be used in the treatment for cancers that are resistant to radiation therapy.

Radiation therapy (RT) is an important component of treatment for both solid tumors and hematological malignancies. It has been shown to improve disease control in the malignancies noted above. In primary brain cancers, esophageal cancers, rectal cancers, breast cancer, prostate cancer, lung cancer, head and neck cancer, lymphomas and leukemia, RT has been shown to improve clinical outcomes [45]. However, the effectiveness of RT can be significantly enhanced by combination with various chemotherapeutic agents that weaken the tumor or initiate initial tumor cell death. The compounds and compositions described herein, such as the compound of Formula (I) (Compound of formula (I)) may be used in this approach as its mechanism as indicated above weakens the tumor strength by blocking the activity of the tumor suppressor let7.

Increased expression of LIN28A and LIN28B has been observed in cancer cells resistant to radiation. In addition, high levels of LIN28 and LIN28B also significantly reduce radiation induced cell in cancer cells. Conversely, the inhibition of LIN28A/B leads to increased sensitivity to radiation. Mechanistically, the inhibition of LIN28 A/B has been shown to decrease the expression of the oncogene RAS as well as DNA associated genes such as RAD51, RAD21, FANCD2 and CDC25, to eventually radiosensitizing the cancer cells [41]. Lin28 has been shown to generate radiation resistance of breast cancer cells via regulation of caspase, H2A.X and let-7 signaling [42]. Accordingly, the compounds and compositions described herein, for example a compound of Formula (I) (Compound of formula (I)), may be used effectively to increase radio-sensitivity to all cancer cells.

In some examples, the compounds and compositions described herein, for example a compound of Formula (I) (Compound of formula (I)), may be used for the treatment of immune and inflammation related diseases. In addition to the involvement in cancer initiation, progression and metastasis, LIN28 A/B have also been shown to be involved in many immune system disorders. Recently, the LIN28 A/B—let7 axis has been shown to be significantly associated with various autoimmune disorders, mediated by an increased production of the proinflammatory cytokine IL-6 that occurs in various autoimmune diseases including rheumatoid arthritis (RA), multiple sclerosis (MS) and systemic lupus erythematosus [34], and targeting IL-6 will be an effective approach in the treatment of several autoimmune diseases [44].

In some examples, a subject may be further treated with an immunotherapy checkpoint inhibitor. Members of the immune checkpoint pathway have been shown to downregulate immune activity against cancer cells. Therefore, therapeutics that function as immune-checkpoint inhibitors have been shown to enhance anti-tumor activity. Most commonly used immune check point inhibitors include antibodies that target the PD1 or PD-L1 that are members of a checkpoint pathway. However, currently, the response to therapeutic antibodies that block the interaction between PD1 and PD-L1 are suboptimal. It has been shown that let-7 has the capability to suppress PD-L1 expression [47]. Therefore, the inhibition of LIN28 with the compounds and compositions as described herein, for example a compound of Formula (I) (Compound of formula (I)), that enhances the expression of mature let-7 may lead to a reduction in PD-L1 and consequently prevent immune evasion by cancer cells. The rescue of let-7 miRNA, through Lin28 inhibition, shown in FIG. 6, will be expanded to explore its potential to reduce PD-L1 pathway and has the capacity to synergize and increase the activity of currently used immune checkpoint inhibitors. Drug combinations may include, but are not limited to, the PD-1 inhibitors Pembrolizumab (Keytruda), Nivolumab (Opdivo) and Cemiplimab (Libtayo) and with the PD-L1 inhibitors Atezolizumab (Tecentriq) and Avelumab (Bavencio) and Durvalumab (lmfinzi).

Studies have shown a link between LIN28 expression and hemoglobin (Hb) synthesis. An inhibition of LIN28 leads to increased expression of let-7 and significantly reduced fetal Hb (HbF) [35]. In some examples, patients with disorders of hemoglobin synthesis may be treated with the compounds and compositions as described herein, for example a compound of Formula (I) (Compound of formula (I)). These disorders include Fanconi anemia, Dyskeratosis congenita, Diamond-Blackfan syndrome, Erythroleukemia, Juvenile Chronic Myeloid Leukemia and Thalassemia.

The term "pharmaceutically effective amount" as used herein refers to the amount of a drug or pharmaceutical agent that will elicit the biological or medical response of a tissue, system, animal or human that is being sought by a researcher or clinician. This amount can be a therapeutically effective amount.

Thus, as used herein, the term "therapeutically effective amount" refers to an amount that is effective for preventing, ameliorating, or treating a disease or disorder (e.g., cancer).

The term "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" as used herein refers to a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation, for example the carrier does not decrease the impact of the agent on the treatment. In other words, a carrier is pharmaceutically inert. The terms "physiologically tolerable carriers" and "biocompatible delivery vehicles" are used interchangeably. Thus, the term "carrier" or "excipient" may refer to a non-toxic solid, semi-solid or liquid filler, diluent. The term includes solvents, dispersion, media, coatings, isotonic agents, and adsorption delaying agents, and the like. The use of such media and agents for pharmaceutically active substances is well known in the art.

As used herein, the term "pharmaceutically-acceptable salts" refers to the conventional nontoxic salts or quaternary ammonium salt. These salts can be prepared in situ in the administration vehicle or the dosage form manufacturing process, or by separately reacting a compound in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In some examples, therapeutic formulations comprising the compounds or compositions as described herein may be prepared for by mixing compounds or compositions having the desired degree of purity with optional physiologically acceptable carriers, excipients or stabilizers, in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

A "pharmaceutical composition" as used herein refers to a chemical or biological composition suitable for administration to a subject. Such compositions may be specifically formulated for administration via one or more of a number of routes, including but not limited to, oral, parenteral, intravenous, intra-arterial, subcutaneous, intra-nasal, sublingual, intra-spinal, intra-cerebroventricular, and the like.

The formulations may conveniently be presented in unit dosage form and may be prepared by any methods well known in the art of pharmacy. Such methods include the step of bringing the active compound into association with a carrier, which may constitute one or more accessory ingredients. In general, the formulations are prepared by uniformly and intimately bringing into association the active compound with liquid carriers or finely divided solid carriers or both, and then if necessary, shaping the product.

The compounds and compositions may be administered to a subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intra-arterial, intra-cardiac, intrathecal, intra-spinal, intracapsular, sub-capsular, intra-orbital, intraperitoneal, intratracheal, subcuticular, intraarticular, subarachnoid, and intra-sternal; by implant of a depot/for example, subcutaneously or intramuscularly.

A skilled worker will be able to determine the appropriate dose for the individual subject by following the instructions on the label. Preparation and dosing schedules for commercially available second therapeutic and other compounds administered in combination with or concomitantly with compounds or compositions described herein may be used according to manufacturers' instructions or determined empirically by the skilled practitioner.

Method of the invention are conveniently practiced by providing the compounds and/or compositions used in such method in the form of a kit. Such kit preferably contains the composition. Such a kit preferably contains instructions for the use thereof.

To gain a better understanding of the invention described herein, the following examples are set forth. It should be understood that these examples are for illustrative purposes only. Therefore, they should not limit the scope of this invention in anyway.

EXAMPLES

Currently, cancer is one of the most common causes for morbidity and mortality across all nations in the world. New therapies and novel treatment protocols are urgently needed for many of the aggressive and treatment resistant cancer subtypes in both children and adults. Recent studies have shown that the LIN28A/B proteins play a crucial role in cancer induction, growth, metastasis, and the generation of treatment resistance in many human malignancies. The mechanisms that have been shown to contribute to LIN28 mediated effects in cancer include the inhibition of the key tumor suppressor microRNA let-7, effect on cellular glucose metabolism, enabling cancer stem cell survival as well as the ability of LIN28 to function as a true oncogene. In addition, the selective expression and alterations cancer cells compared to normal developmentally mature cells prove a novel opportunity to develop effective targeted therapeutic agents to treat a wide spectrum of aggressive and treatment resistant cancers.

We describe the generation of a novel small molecule chemical inhibitor that binds and blocks the activity of LIN28A/B. Also described are the tools, applications and methods by which the molecule was created by the inventors and the specific instructions generated for the synthesis of the active molecule, hereby named Compound of formula (I) (ie. the compound of Formula (I)). Finally, we describe the various assays conducted and their findings that validate and substantiate the specificity, activity and tolerability by normal cells.

Methodology

1. Rationalized Design of Lin28-Selective Molecule (FIG. 1) We performed a comprehensive study of in silico binding preferences present in the X-ray crystal structure of Lin28A and its catalytic site described previously in the literature (PDB ID 5UDZ) [3]. This is a highly selective binding site for GGAG strand of pre-let-7 microRNA showing affinity for the Zinc Knuckle Domain (ZKD) and, catalytic residues such as His148 and Try140. It has been shown that the mutation of GGAG to GGAU or UGAG leads to disruption in the LIN28 and pre-let-7 complex and could be utilized for therapeutic targeting [3]. We investigated the LIN28A residues responsible for interaction with GGAG hair loop region. Indeed, His148 and Try140 of Lin28A were present at ≤3 Å distances around $\underline{G}$GAG and His162 was involved in the interaction with G$\overline{G}$$\underline{AG}$ which also contained a Cys residue hydrophobic corner. In order to strategize the disruption in binding between His148/Tyr140 and $\underline{G}$GAG, we introduced a benzamide group (first part of the molecule) which would potentially interact primarily with amino and hydroxyl side chains of His148 and Tyr140, and further prevent the pre-let-7 from binding in that region. This benzamide moiety also displayed tighter conformation with the Zinc metal, which was expected because benzamide-like groups are known Zinc-binders. Similarly, the final part of the molecule contained Benzothiozole moiety which would bind to the LIN28A pocket containing His162 (where GGA$\underline{G}$ is known to bind) and Cys residues. The disulphide bonding was observed between the benzothiazole and the Lin28A Cys residues. The middle part of the molecule was introduced with Histidine and Isoleucine moieties in order to form a bend in the structure, thus replicating the pre-let-7 hair loop conformation. This bend in small molecule was contributed by Histidine and Isoleucine facing away from each other due to the hydrophobic load towards the benzothiazole group.

Once the molecule was finalized based on the binding determinant requirements of Lin28A, we performed receptor-ligand docking of this lead molecule with Lin28A using the AutoDock Vina and BIOVIA Discovery Studio platforms based on their established drug binding tutorials. After repeated adjustments and residue replacements in small molecules, we observed greater binding with Compound of formula (I) that contained peptide-like backbone, with either terminus chemically end-capped with functional alternators (benzamide and benzothiazole moieties). The overall binding affinity of Compound of formula (I) with LIN28A was −15.5 kcal/mol.

2. Steps in Compound of Formula (I) Synthesis

Figure 2:
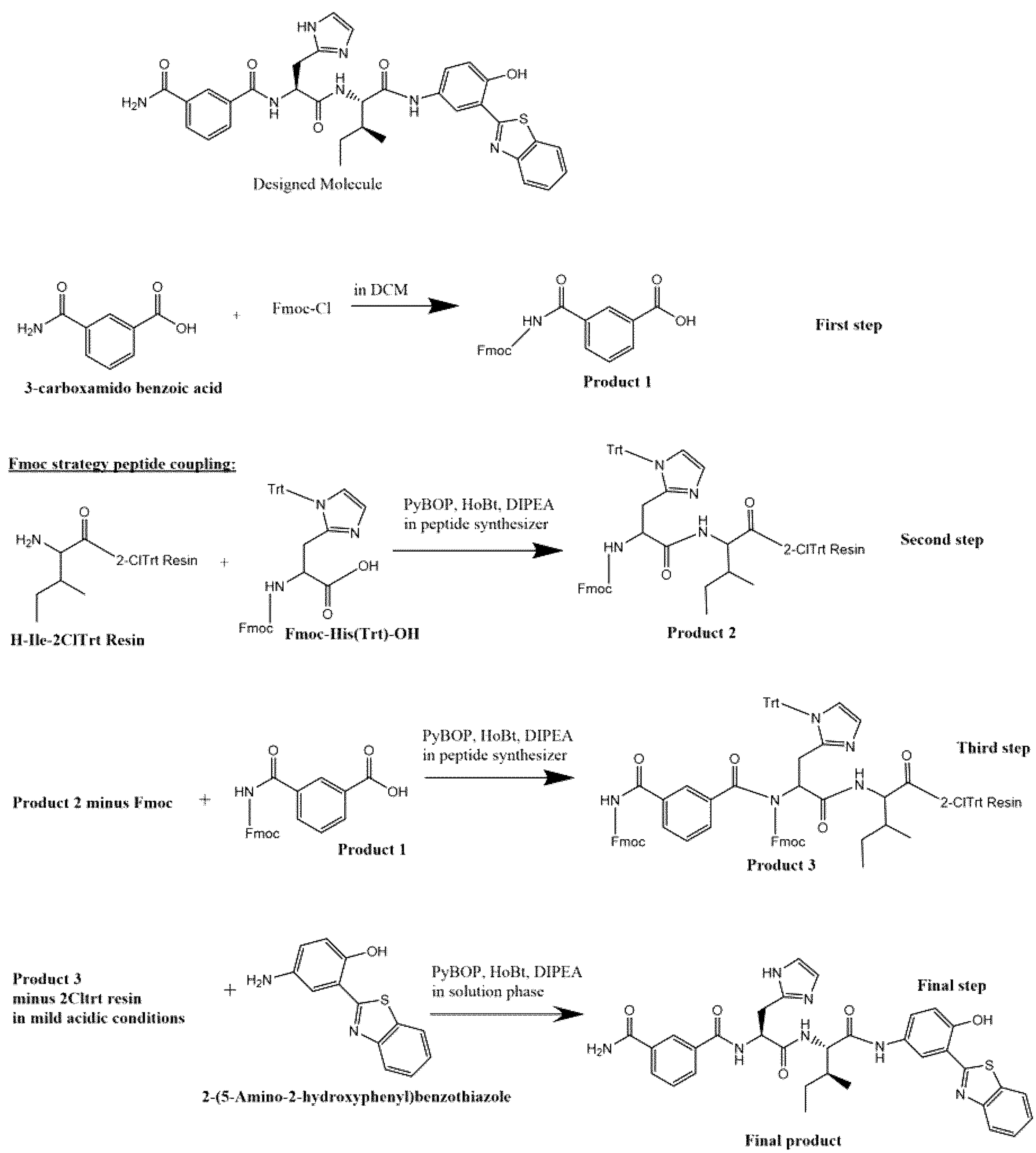
FIG. 2: depicts a specific process of synthesis of Compound of formula (I). This synthetic route produced two isomers with the same molecular compositions. These isomers were present in the same mixture, therefore labeled as P1+P2.
Figure 3:
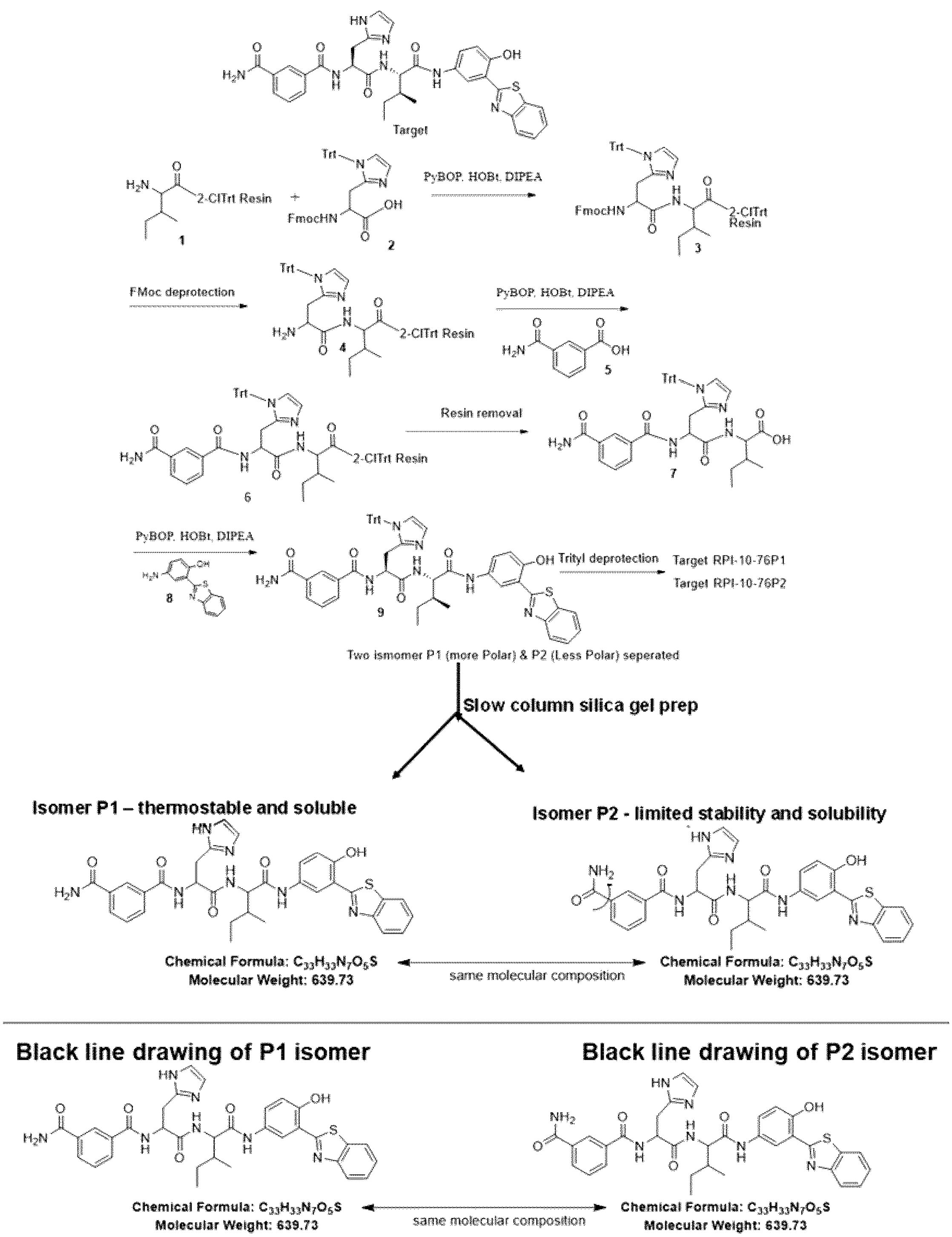
FIG. 3: depicts the synthesis of P1 and P2. Compound of formula (I) underwent comprehensive purification by a slow column using normal silica gel. The two isomers were separated at the trityl protected state (compound 9 in FIG. 3).

FIGS. 2, 3 and 4; depicts the specific process of synthesis of Compound of formula (I) P1.

The final product, P1 isomer was purified in C18 column using RP-HPLC and the greenish-yellow compound was freeze dried. The drug displayed solubility in DMSO at 10 mM and in water/PBS/culture medium at 50 μM concentrations.

3. HEK 293 T Stable Cell Line Expressing EGFP-Tagged Lin28A

This method was adapted from Roos et al (2016) [4]. HEK 293-T cells (ATCC) were cultured as monolayers in DMEM GlutaMAX™-1 (Cat #31966-021, Gibco®, Life Technologies) supplemented with 10% of FBS (fetal bovine serum). Stable EGFP-Lin28A HEK 293-T cells were cultured as monolayers in DMEM supplemented with 10% of FBS (fetal bovine serum) and 0.5 mg/ml Geneticin G418 (10131-035, Life Technologies). Transfections were performed according to the manufacturer's protocol with Oligofectamine 2000 (12252-011, Invitrogen, Life Technologies) for siRNAs and JetPEI (101-10, Polyplus transfections) was used for plasmid DNA. For cellular treatment the small molecules were dissolved in DMSO resulting in a maximum 1% DMSO content in the cell growth media.

160'000 HEK 293 T cells were seeded per well in 6 well plates and transfected with 320 ng pEGFP-C2-Lin28A plasmid according to the experimental setup with the reagents described above and cells were allowed to recover for 48h. To start selection, cell growth medium was changed by adding selective medium DMEM GlutaMAXTM-1 containing 0.5 mg/ml Geneticin and cells were reseeded in 6 cm diameter dishes. Geneticin concentration of medium was increased two days later to 1 mg/ml and antibiotics containing media was replaced every second day for two more weeks. Subsequently, selective antibiotic concentration in the medium was decreased to 0.5 mg/ml and positive clones were selected by fluorescent microscopy transferring positive clones to individual wells of a 96 well plate. Antibiotic selection was maintained for one further week. The EGFP-lin28A| expressing cells were sorted using Fluorescence Activated Cell Sorting (FACS). Finally, larger colonies of individual clones were analyzed for expression levels of EGFP-Lin28A by performing the FRET assay.

4. Synthesis and Optimization of FRET Assay Constituents:

Based on specific quencher labelling instructions and successful FRET assessments for identification of Lin28 inhibitors [4], truncated pre-let-7a miRNA labelled with a quencher molecule—black hole quencher 1 (BHQ-1) (acceptor) at position 19 [known as 19B-let-7a] were custom synthesized from BioSyn Life Sciences.

The FRET assay contained N-terminally EGFP-tagged Lin28B as donor and a truncated prelet-7a-2 as acceptor, which is labeled BHQ-1 quencher. Assays were carried out on a spectrofluorometer (PTI, Edison New Jersey) in a 384-well plate format. Briefly, EGFP-Lin28A lysate diluted with binding buffer (1:10) was mixed with various concentrations of labeled pre-let-7a-2 (0, 0.01, 0.02, 0.05, 0.1, 0.25, 0.5, 1 and 2 μM) individually. Solutions were incubated for 30-45 min and their EGFP fluorescence spectra were acquired at 520 nm after the excitation of the sample at 485 nm.

Plates: Perkin Elmer, ProxiPlate™ #6008260
Mode: Fluorescence Top Reading
Flash frequency: 100 Hz
Number of flashes: 20
Integration time: 20 μs
Excitation wavelength: 485 nm
Excitation bandwidth: 5 nm
Emission wavelength: 520 nm
Emission bandwidth: 5 nm 5. Compound Screen:

FRET system (EGFP-Lin28A and 19B-let7a) treated with DMSO was used as positive control. 19B-let7a concentration capable of causing alteration EGFP FRET by 90% was chosen for compound screening. The EGFP-Lin28A donor (1:10 dilution with binding buffer) and 19B-let7a acceptor mixture (Total 14 μl) were incubated for 30 minutes. Compound of formula (I) was subsequently added (4 μl of experimental concentrations) and incubated for further 30 minutes. The FRET measurements were obtained from the optimized fluorescence parameter. The optimization and compound evaluation were followed in triplicate. The average signal intensity and background fluorescence were corrected with compound self-fluorescence with and without binding buffer.

6. Western Blotting

The proteins were extracted from the same samples as the RNA using the RIPA lysis buffer. The protein extracts (20 μg) were run on 10% SDS-PAGE and transferred on a nitrocellulose blotting membrane 0.22 μm (GE Healthcare) using the Trans-Blot® SD semi-dry transfer devise (Biorad). The proteins were detected using the anti-Lin28A antibody (#8706; Cell Signaling Technology), anti-Lin28B antibody (#11965, Cell Signaling Technology) the anti-beta-actin antibody at respectively 1:2000, 1:2000 and 1:5000 dilutions. The western blots were revealed using the Clarity Western ECL substrate (Biorad) on a ChemiDoc MP imager (Biorad).

7. qRT-PCR

Total RNA was extracted using the RNeasy kit (74104, Qiagen). TaqMan® qRT-PCR was performed using standard reagents from Life Technologies (TaqMan® MicroRNA Assay: hsa-let-7a: 000377). The RT was performed using the TaqMan® primers from MicroRNA Assays and the TaqMan® MicroRNA Reverse Transcription Kit (4366596, Life technologies) with 20 ng total RNA. The PCR was performed in a LightCycler 480 instrument with GoTaq® Probe qPCR Master mix (A6102, Promega) according to the manufacturer's protocol. Each reaction was carried out in three technical replicates.

Flow Cytometry

The method for Propidium Iodide (PI) based cell cycle analysis was performed as per the instructions given by the manufacturer (AB139418; Abcam). Briefly NT-2 cells treated with Compound of formula (I) versions were harvested in single cell suspensions with each experimental condition containing two million cells, fixed in 66% Ethanol overnight at 4° C. The ethanol was removed thoroughly by centrifugation, followed by rehydration of cells in PBS with a repeat of centrifugation. Cells were stained in PI (1%) and RNase solution (1%) in PBS for 30 minutes at 37° C. in the dark. The cells were analyzed immediately on the Flow Cytometer.

Generation of Tumor Xenografts for In Vivo Testing of Compound of Formula (I)

All animal procedures were carried out in accordance with the guidelines of the Canadian Council on Animal Care and the NIH guidelines on the care and use of laboratory animals. All protocols were reviewed and approved by the Animal Care Committee of the University of Calgary (Protocol approval number: AC21-0147). Six- to eight-week-old female or male CB17 severe combined immunodeficiency (SCID) mice (Charles River Laboratories, Saint-Constant, QC, Canada) were subcutaneously injected in the right flank with $3\times10^6$ YP-MEL or NT-2 cells suspended in 0.1 mL sterile PBS. After tumor injection, animals with detectable tumor growth of at least 50 $mm^2$ were randomized into groups. The groups were treated with either 0.1% DMSO: PBS vehicle or 4 mg/kg of Compound of formula (I) dissolved in the vehicle, intraperitoneally (I.P), orally (P.O) or intravenously (I.V). Animals and respective cages were monitored for food and bedding supplies daily; doses were injected every 2 days and tumor areas were measured with a Vernier caliper (prior to each treatment cycle). When vehicle treated tumors reached the defined endpoint of 225 $mm^2$, every mouse in the group were euthanized. Tumors were excised and immediately imaged and processed for western blotting or fixed in paraformaldehyde for toxicology evaluation. (A)

Figure 1:
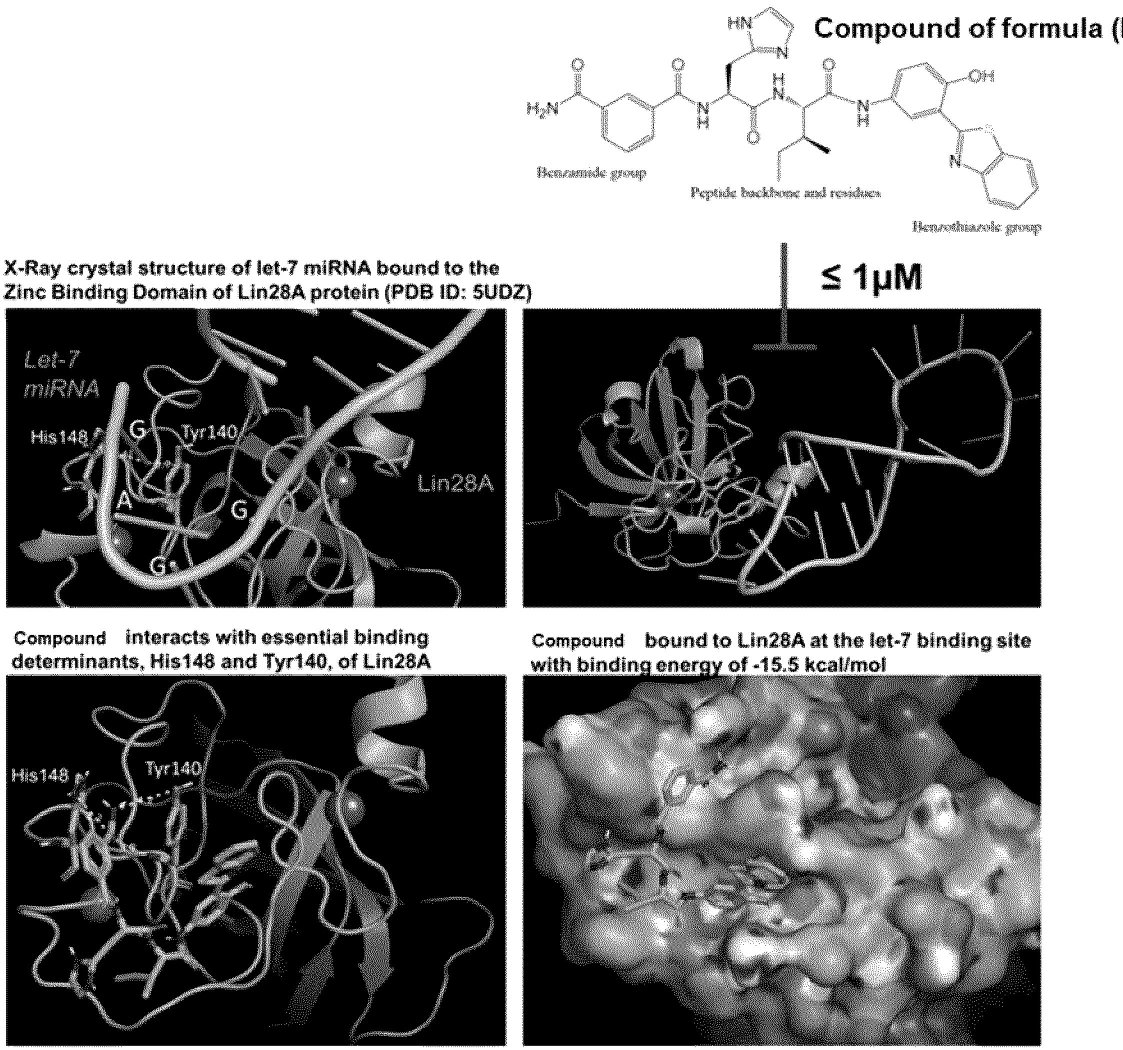
FIG. 1: Rationalized structure-based design of LIN28-selective small molecule inhibitor. The X-Ray crystal structure of Lin28A-let-7 bound complex (PDB ID: 5UDZ) was utilized for the study and exploitation of let-7 binding grove on Lin28A surface. The hair pin conformation of the let-7 binding determinant strands (GGAG) present at the Zinc Knuckle Domain (ZKD) of Lin28A was initially studied for designing of structural replica, followed by introduction of small molecule residues capable of disrupting the catalytic binding present between Lin28A and let-7 microRNA. The designed small molecule, named Compound of formula (I), displayed a strong binding (binding energy: −15.5 kcal/mol) towards the ZKD region of Lin28A. Compound of formula (I) bound strongly to the Lin28A residues His148 and Tyr140 which have previously been known to accommodate the let-7 tumor suppressor.

FIG. 1: Rationalized structure-based design of LIN28-selective small molecule inhibitor. The X-Ray crystal structure of Lin28A-let-7 bound complex (PDB ID: 5UDZ) was utilized for the study and exploitation of let-7 binding grove on Lin28A surface. The hair pin conformation of the let-7 binding determinant strands (GGAG) present at the Zinc Knuckle Domain (ZKD) of Lin28A was initially studied for designing of structural replica, followed by introduction of small molecule residues capable of disrupting the catalytic binding present between Lin28A and let-7 microRNA. The designed small molecule, named Compound of formula (I), displayed a strong binding (binding energy: −15.5 kcal/mol) towards the ZKD region of Lin28A. Compound of formula (I) bound strongly to the Lin28A residues His148 and Tyr140 which have previously been known to accommodate the let-7 tumor suppressor.

FIG. 2 depicts a specific process of synthesis of Compound of formula (I). This synthetic route produced two isomers with the same molecular compositions. These isomers were present in the same mixture, therefore labeled as P1+P2.

FIG. 3: depicts the synthesis of P1 and P2. Compound of formula (I) underwent comprehensive purification by a slow column using normal silica gel. The two isomers were separated at the trityl protected state (compound 9 in FIG. 3). The deprotection of Trityl was achieved separately to obtain P1 and P2 isomers. The one-sided arrow in the P2 isomer shows the rotation or inter-substitution of benzamide associated amine and carbonyl functional groups. This molecular re-arrangement of P2 isomer may have lead to subsequent modification of 3D conformation, potentially causing a reduced exposure of its solvent accessible surfaces. The presence of these purified isomers were analytically confirmed using Nuclear Magnetic Resonance (NMR) and Mass Spectrometry. FIG. 4: Compound of formula (I) structure and elemental composition.

FIG. 5: Compound of formula (I) mixture, containing the two isomers (P1+P2) causes significant reduction in Lin28A protein from 5 μM onwards, in a panel of endogenously LIN28 expressing cancer cell models. This novel molecule inhibits LIN28B at 50 μM, demonstrating 10-fold binding differential between its affinity for LIN28A relative to LIN28B. LIN28A and LIN28B expression profile in pediatric CNS cancer cell lines, 96-hr post-treatment with Compound of formula (I). SDS-PAGE on 10% polyacrylamide gel of total cell lysates from untreated cells harvested at 80-90% confluency. Samples loaded with volumes for 20 μg protein. LIN28A and LIN28B proteins were detected using the anti-LIN28A antibody (#8706; Cell Signaling Technology) and anti-LIN28B antibody (#11965; Cell Signaling Technology) at 1:2000 dilutions. T47D: adult breast cancer (LIN28A expressing); YPMEL: malignant melanoma derived from Neurocutaneous Melanosis (NCM) (Lin28A and Lin28B expressing); BT-12: pediatric atypical-teratoid rhabdoid tumor (AT/RT).

FIG. 6: Cells were cultured in the presence of the Compound of formula (I) (P1+P2) at increasing concentrations and cell viability was evaluated using Alamar Blue dye and measurement at Excitation of 550 nm and Emission of 590 nm. All the data shown are representative of three replicates. LIN28A-positive cancer cell models displayed heightened sensitivity to Compound of formula (I), relative to LIN28B-expressing cancer cell models. Whereas, normal lymphocytes and fibroblast cells (LIN28-negative) lacked sensitivity to Compound of formula (I) at treated dosages, over 96-120 hour. IC50 concentrations of Compound of formula (I) in panel of cancer cell lines expressing Lin28A ranged at ≤1 μM (cell lines A549, YP-MEL, T47D), where cancer cells expressing only Lin28B demonstrated IC50 at 100 μM (cell lines IMR5 and BT12). LIN28A and LIN28B expression in the presence of Compound of formula (I) correlates with the sensitivity of cells to this inhibitor.

FIG. 7A-C. To determine the differences in the biological activity of the two isomers (P1+P2) of Compound of formula (I), we tested the effects of purified and separated P1 and P2 isomers on the protein expression of Lin28A and Lin28B. (A) YP-MEL (NCM). (B) BT-37 (AT/RT). (C) NT-2 (NTERA) (Testicular cancer). The western blotting of NCM, AT/RT and testicular cells for Lin28 proteins demonstrated that the most soluble(soluble until 100 mg/ml in DMSO) version of Compound of formula (I) called P1 was capable of inhibiting Lin28A selectively from 1 μM onwards whereas, the less soluble version P2 (insoluble at 1 mg/ml in DMSO) had no effect on the expression levels of Lin28A in the tested cell models. Lin28B expression remained unaltered from the treatments of P1 and P2 at the tested dosages. It was noted that the P1 version of Compound of formula (I) was 5 times more selective that the crude mixture containing P1+P2, as observed in FIG. 5.

FIG. 8A-F. Cells were cultured in the presence of the Compound of formula (I) (versions P1, P2 or P1+P2 at equipotent doses) at increasing concentrations and cell viability was evaluated using Alamar Blue dye and measurement at Excitation of 550 nm and Emission of 590 nm. All the data shown are representative of three replicates. LIN28A-positive cancer cell models displayed heightened sensitivity to Compound of formula (I), relative to LIN28B-expressing cancer cell models. A. NT-2 cell viability. B. YP-MEL cell viability. C. WI-38 cell viability. D. T47D cell viability. E. BT-12 cell viability. F. summary of Lin28A and Lin28B status.

FIG. 9. NT-2, testicular cancer cells, were incubated with Compound of formula (I) isomers for 24h and subjected to Flow Cytometric analysis to determine the alterations in cancer cell cycle. In the first 24h, the P1 version of Compound of formula (I) triggered apoptosis in NT-2 testicular cancer cells where approximately 10% of the total cell count had undergone cell death This finding further proved the effectiveness of isomer P1 in causing cancer cell death. As expected, the P1+P2 version was only half as effective in triggering cancer cell death. P2, however, failed to cause any significant changes in cancer cell viability. Therefore, only the P1 isomer of Compound of formula (I) was investigated further to determine its in vitro and in vivo efficacy.

FIG. 10: FRET optimization of BHQ1-tagged pre-let-7a [19B-let7a] (acceptor) mediated concentration-dependent quenching of EGFP-tagged Lin28A (donor). 19B-let7a at 100 nM, displayed 90% quenching of EGFP-lin28A and was chosen for FRET screening with P1 ver. The introduction of Compound of formula (I) resulted in a dose-dependent displacement of recombinant BHQ1-pre-let7a and EGFP-Lin28A bound complexes displaying a reduction in FRET by 70% at 1 μM as compared to c1632, a known pan-Lin28 inhibitor, which displayed equivalent FRET reduction at 100 μM FIG. 11: Compound of formula (I) lead to successful rescue of pre-let-7a and their maturation to miRNA let-7a tumor suppressor, only at 1 μM. Pharmacological inhibition of Lin28A using Compound of formula (I) lead to increase in the expression of let-7a miRNA tumor suppressor (Taqman MicroRNA Assay: has-let-7a: 000377) in YP- MEL, T47D, A549 (Adult adenocarcinoma; both LIN28A and LIN28B expressing) cells, measured by Taqman miRNA qRT-PCR. Whereas, Lin28B expressing BT-12 demonstrated only minor upregulation of let-7a suggesting a therapeutic concentration window between the preference of Compound of formula (I) for Lin28A versus Lin28B Change in miRNA expression levels were relative to noncoding RNU6B.

FIG. 12. Dose-dependent effect of Compound of formula (I) on the stem cell tumor spheres, in the presence of LIF—a pluripotency supplement used for maintenance of stem cell population (Panel A). As determined by western blotting, Compound of formula (I) begins to halt the expression of stemness markers (Nestin, LIN28A, Oct-4) and induces elevation of differentiation markers (GFAP), from 1 μM onwards (Panel B).

FIGS. 13A&B. Female SCID YP-MEL NCM tumor bearing mice treated with 4 mg/kg Compound of formula (I) (P1 version) intraperitoneally (I.P). (A.) Compound of formula (I) significantly reduced the growth of NCM tumors with every dose. (B) Tumor areas were measured with a Vernier caliper (prior to each treatment cycle). Animals were euthanized when the control (0.1% DMSO:PBS) treated mice reached the defined endpoint of 225 $mm^2$. Data representative of at least 5 independent experiments.

FIG. 14A-C. Male SCID NT-2 testicular tumor bearing mice treated with 4 mg/kg Compound of formula (I) (P1 version) via oral route of administration (P.O). Compound of formula (I) significantly reduced the growth of NT-2 tumors with every dose. Tumor areas were measured with a Vernier caliper (prior to each treatment cycle). Animals were euthanized when the control (0.1% DMSO:PBS) treated mice reached the defined endpoint of 225 $mm^2$. Data representative of at least 5 independent experiments. (A) shows photographs of treatment versus control. (B) is a graph depicting percentage change of tumour volume versus days after the first treatment. (C) is a graph depicting percentage survival versus days after the first treatment.

FIG. 15A-D. Male SCID NT-2 testicular tumor bearing mice treated with 4 mg/kg Compound of formula (I) (P1 version) via intraperitoneal route of administration (I.P). Compound of formula (I) significantly reduced the growth of NT-2 tumors with every dose, and at least 50% of the treated animals survived tumor-free for 120 days. Tumor areas were measured with a Vernier caliper (prior to each treatment cycle). Animals were euthanized when the control (0.1% DMSO:PBS) treated mice reached the defined endpoint of 225 $mm^2$. Data representative of at least 5 independent experiments. (A) shows photographs of treatment versus control. (B) is a graph depicting percentage of tumour size versus days after the first treatment. (C) is a graph depicting percentage survival versus days after the first treatment. (D) is a photograph showing excised tumours.

FIGS. 16A&B. Male SCID NT-2 testicular tumor bearing mice treated with 4 mg/kg Compound of formula (I) (P1 isomer) via intravenous route of administration (I.V). Compound of formula (I) significantly reduced the growth of NT-2 tumors with every dose and in some cases showed complete shrinkage with only 4 doses. Tumor areas were measured with a Vernier caliper (prior to each treatment cycle). Animals were euthanized when the control (0.1% DMSO:PBS) treated mice reached the defined endpoint of 225 $mm^2$. Data representative of at least 5 independent experiments. (A) is a photograph showing excised tumours. (B) is graph depicting percentage of tumor size versus number of treatments.

FIG. 17A-G: Analytical detection of Compound of formula (I) isomers using 1D NMR and purified P1 isomer of Compound of formula (I) detected using Liquid Chromatography Mass Spectrometry (LCMS). (17A-C) is the H1-1D NMR profile of purified P1 isomer of Compound of formula (I) dissolved in DMSO at 2.49 ppm (parts per million) at 27° C. using 400 MHz instrument. (17D-F) is the H1-1D NMR profile of purified P2 isomer of Compound of formula (I) dissolved in DMSO at 2.49 ppm (parts per million) at 27° C. using 400 MHz instrument. FIG. 17G is the mass detection of P1 Compound of formula (I) showing spectrometry ionized signal of molecular mass 640.2 $[M+H]^+$, detected using LCMS.

REFERENCES

1. Ambros, V. and H.R. Horvitz, Heterochronic mutants of the nematode *Caenorhabditis elegans*. Science, 1984. 226(4673): p. 409-16.
2. Moss, E. G., R. C. Lee, and V. Ambros, The cold shock domain protein LIN-28 controls developmental timing in *C. elegans* and is regulated by the lin-4 RNA. Cell, 1997. 88(5): p. 637-46.
3. Zhu, H., et al., The Lin28/let-7 axis regulates glucose metabolism. Cell, 2011. 147(1): p. 81-94.
4. Yuan, J., et al., Lin28b reprograms adult bone marrow hematopoietic progenitors to mediate fetal-like lymphopoiesis. Science, 2012. 335(6073): p. 1195-200.
5. Polesskaya, A., et al., Lin-28 binds IGF-2 mRNA and participates in skeletal myogenesis by increasing translation efficiency. Genes Dev, 2007. 21(9): p. 1125-38.
6. West, J. A., et al., A role for Lin28 in primordial germ-cell development and germ-cell malignancy. Nature, 2009. 460(7257): p. 909-13.
7. Corrigendum: Genetic Analysis of the Role of the Reprogramming Gene LIN-28 in Human Embryonic Stem Cells. Stem Cells, 2015. 33(7): p. 2360.
8. Viswanathan, S. R., et al., Lin28 promotes transformation and is associated with advanced human malignancies. Nat Genet, 2009. 41(7): p. 843-8.
9. Balzeau, J., et al., The LIN28/let-7 Pathway in Cancer. Front Genet, 2017. 8: p. 31.
10. Piskounova, E., et al., Lin28A and Lin28B inhibit let-7 microRNA biogenesis by distinct mechanisms. Cell, 2011. 147(5): p. 1066-79.
11. Nguyen, L. H. and H. Zhu, Lin28 and let-7 in cell metabolism and cancer. Transl Pediatr, 2015. 4(1): p. 4-11.
12. Farzaneh, M., F. Attari, and S. E. Khoshnam, Concise Review: LIN28/let-7 Signaling, a Critical Double-Negative Feedback Loop During Pluripotency, Reprogramming, and Tumorigenicity. Cell Reprogram, 2017. 19(5): p. 289-293.
13. Roush, S. and F. J. Slack, The let-7 family of microRNAs. Trends Cell Biol, 2008. 18(10): p. 505-16.
14. Zhang, J., et al., Prognostic value of Lin28A and Lin28B in various human malignancies: a systematic review and meta-analysis. Cancer Cell Int, 2019. 19: p. 79.
15. Kim, S. K., et al., SET7/9 methylation of the pluripotency factor LIN28A is a nucleolar localization mechanism that blocks let-7 biogenesis in human ESCs. Cell Stem Cell, 2014. 15(6): p. 735-49.
16. Nam, Y., et al., Molecular basis for interaction of let-7 microRNAs with Lin28. Cell, 2011. 147(5): p. 1080-91.
17. Liu, Y., et al., Lin28 induces epithelial-to-mesenchymal transition and stemness via downregulation of let-7a in breast cancer cells. PLoS One, 2013. 8(12): p. e83083.

18. Feng, C., et al., Lin28 regulates HER2 and promotes malignancy through multiple mechanisms. Cell Cycle, 2012. 11(13): p. 2486-94.

19. Ma, W., et al., Lin28 regulates BMP4 and functions with Oct4 to affect ovarian tumor microenvironment. Cell Cycle, 2013. 12(1): p. 88-97.

20. Lu, L., et al., Pluripotent factor lin-28 and its homologue lin-28b in epithelial ovarian cancer and their associations with disease outcomes and expression of let-7a and IGF-II. Eur J Cancer, 2009. 45(12): p. 2212-8.

21. King, C. E., et al., LIN28B promotes colon cancer progression and metastasis. Cancer Res, 2011. 71(12): p. 4260-8.

22. Faria, A. M., et al., Expression of LIN28 and its regulatory microRNAs in adult adrenocortical cancer. Clin Endocrinol (Oxf), 2015. 82(4): p. 481-8.

23. Nguyen, L. H., et al., Lin28b is sufficient to drive liver cancer and necessary for its maintenance in murine models. Cancer Cell, 2014. 26(2): p. 248-61.

24. Wang, D., et al., The pluripotency factor LIN28B is involved in oral carcinogenesis and associates with tumor aggressiveness and unfavorable prognosis. Cancer Cell Int, 2015. 15: p. 99.

25. Wu, T., et al., Increased expression of Lin28B associates with poor prognosis in patients with oral squamous cell carcinoma. PLoS One, 2013. 8(12): p. e83869.

26. Kim, Y. J., et al., Immunohistochemical study identifying prognostic biomolecular markers in nasopharyngeal carcinoma treated by radiotherapy. Head Neck, 2011. 33(10): p. 1458-66.

27. Hamano, R., et al., High expression of Lin28 is associated with tumour aggressiveness and poor prognosis of patients in oesophagus cancer. Br J Cancer, 2012. 106(8): p. 1415-23.

28. Qin, R., et al., LIN28 is involved in glioma carcinogenesis and predicts outcomes of glioblastoma multiforme patients. PLoS One, 2014. 9(1): p. e86446.

29. Molenaar, J. J., et al., LIN28B induces neuroblastoma and enhances MYCN levels via let-7 suppression. Nat Genet, 2012. 44(11): p. 1199-206.

30. Korshunov, A., et al., LIN28A immunoreactivity is a potent diagnostic marker of embryonal tumor with multilayered rosettes (ETMR). Acta Neuropathol, 2012. 124 (6): p. 875-81.

31. Urbach, A., et al., Lin28 sustains early renal progenitors and induces Wilms tumor. Genes Dev, 2014. 28(9): p. 971-82.

32. Beachy, S. H., et al., Enforced expression of Lin28b leads to impaired T-cell development, release of inflammatory cytokines, and peripheral T-cell lymphoma. Blood, 2012. 120(5): p. 1048-59.

33. Chen, A. X., et al., Germline genetic variants disturbing the Let-7/LIN28 double-negative feedback loop alter breast cancer susceptibility. PLoS Genet, 2011. 7(9): p. e1002259.

34. Zhou, J., et al. LIN28/LIN28B: an emerging oncogenic driver in cancer stem cells. Int J Biochem Cell Biol, 2013. 45(5): p. 973-8.

35. Lee, Y. T, et al. Lin28B-mediated expression of fetal hemoglobin and production of fetal-like erythrocytes from adult human erythroblasts ex vivo. Blood, 2013. 122(6):p. 1034-41.

36. Wang, L., et al., LIN28 Zinc Knuckle Domain Is Required and Sufficient to Induce let-7 Oligouridylation. Cell Rep, 2017. 18(11): p. 2664-2675.

37. Roos, M., et al., A Small-Molecule Inhibitor of Lin28. ACS Chem Biol, 2016. 11(10): p. 2773-2781.

38. Zhuo Z, et al. LIN28A gene polymorphisms confer Wilms tumour susceptibility: A four-centre case-control study. J Cell Mol Med. 2019 October; 23(10):7105-7110]

39. Balzeau J, et al. The LIN28/let-7 Pathway in Cancer. Front Genet. 2017 Mar. 28; 8:31. doi: 10.3389/fgene.2017.00031.

40. Feng C, et al. Cell Cycle. 2012 Jul. 1; 11(13):2486-94.

41. McCarty, M. F. et al. Metformin may antagonize Lin28 and/or Lin28B activity, thereby boosting let-7 levels and antagonizing cancer progression. Med. Hypotheses 78, 262-269.

42. Xiong H, et al. Oncogenic mechanisms of Lin28 in breast cancer: new functions and therapeutic opportunities. Oncotarget. 2017; 8(15):25721-25735

43. Wang L, et al. Lin28 mediates radiation resistance of breast cancer cells via regulation of caspase, H2A. X and Let-7 signaling. PLoS One. 2013; 8:e67373.

44. Geng L, et al. Reduced Let-7f in Bone Marrow-Derived Mesenchymal Stem Cells Triggers Treg/Th17 Imbalance in Patients With Systemic Lupus Erythematosus. Front Immunol. 2020 Feb. 18; 11:233.

45. Yamoah K, et al. Radiation Therapy Intensification for Solid Tumors: A Systematic Review of Randomized Trials. Int J Radiat Oncol Biol Phys. 2015; 93(4):737-745.

46. https://www.amboss.com/us/knowledge/Chemotherapeutic_agents

47. Chen Y, et al. LIN28/let-7/PD-L1 Pathway as a Target for Cancer Immunotherapy. Cancer Immunol Res. 2019 March; 7(3):487-497.

48. McDaniel, et al. Lin28 and let-7: roles and regulation in liver diseases. Am J Physiol Gartointest Liver Physiol. 2016 May; 310(10):G757-G765.

The embodiments described herein are intended to be examples only. Alterations, modifications and variations can be effected to the particular embodiments by those of skill in the art. The scope of the claims should not be limited by the particular embodiments set forth herein, but should be construed in a manner consistent with the specification as a whole.

All publications, patents and patent applications mentioned in this Specification are indicative of the level of skill those skilled in the art to which this invention pertains and are herein incorporated by reference to the same extent as if each individual publication patent, or patent application was specifically and individually indicated to be incorporated by reference.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. A compound of Formula (I), or a tautomer, pharmaceutically acceptable salt, or solvate thereof:

(I)

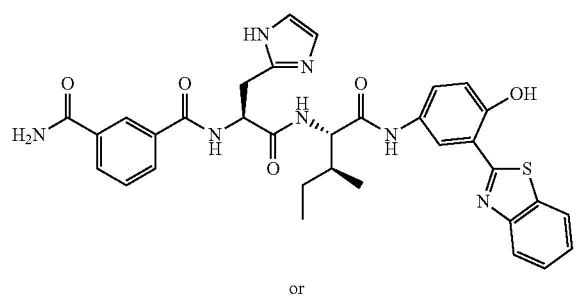

;

or a tautomer of Formula (P2):

(P2)

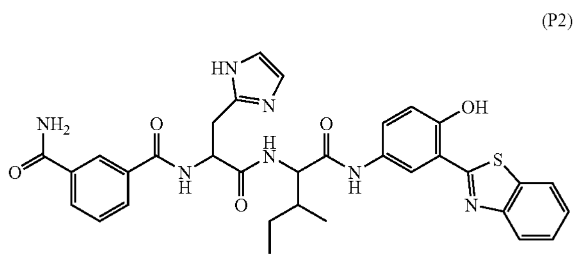

a compound of Formula (I-B), or a tautomer, pharmaceutically acceptable salt, or solvate thereof:

(I-B)

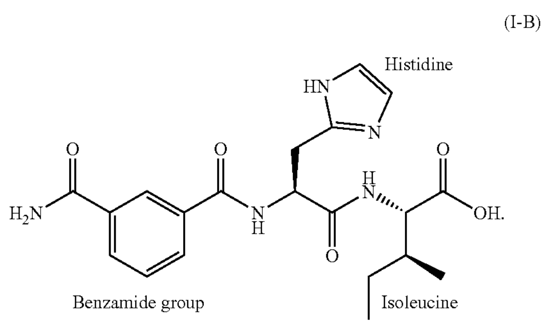

2. The compound claim 1, wherein the compound of Formula (I) comprises a tautomer of Formula (P2)

(P2)

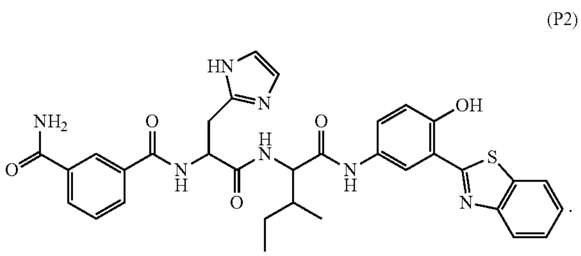 [SMILES: CCC(C)C(NC(=O)C(Cc1ncc[nH]1)NC(=O)c1cccc(C(N)=O)c1)C(=O)Nc1ccc(O)c(-c2nc3ccccc3s2)c1]

3. A composition comprising a compound of claim 1, and a pharmaceutically acceptable carrier, diluent, or vehicle.

4. A method of treating a subject with cancer, at risk of developing cancer, or suspected of having a cancer, comprising: administering a therapeutically effective amount of a composition of claim 3.

5. The method of claim 4, wherein the cancer is Acute Myeloid Leukemia (AML), Atypical teratoid/rhabdoid tumor, Embryonal tumors with multi-layered rosettes (ETMR), Brain cancers (Pediatric and adult), Breast cancer, Cervical cancer, Sarcomas, Chronic myeloid leukemia (CML), Colon cancer, Gastric cancer, Germ cell tumors, Yolk sac tumors, Oesophageal cancer, rectal cancers, Glioblastoma multiforme, Glioma (pediatric and adult), Liver cancer, Medulloblastoma, Multiple Myeloma, Neuroblastoma, Oral squamous cell carcinoma, Ovarian primitive germ cell tumors, Ovarian cancers, Pheochromocytomas, Paragangliomas, Primitive neuroectodermal tumors, Prostate cancer, Testicular germ cell tumors, Wilms tumor, Pediatric neurocutaneous melanosis (NCM) associated CNS tumor, adenocarcinoma, or testicular cancer.

6. The method of claim 4, wherein the subject a pediatric subject or an adult subject, wherein said subject is a human.

7. The method of claim 4, wherein the cells of said cancer overexpress LIN28A protein and/or LIN28B protein, compared to a control.

8. The method of claim 4, wherein the cells of said cancer comprise reduced levels of let-7 microRNA, compared to a control.

9. The method of claim 4, wherein the LIN28A gene and/or LIN28B gene within said cells of said cancer comprise mutations and/or or SNPs amplifications.

10. The method of claim 4, wherein the cancer is resistant to chemotherapy and/or radiation therapy.

11. The method of claim 4, further comprising treatment with radiation therapy.

12. The method of claim 4, further comprising treatment with a chemotherapeutic agent.

13. The method of claim 12, wherein said chemotherapeutic agent is one or more of Antimetabolites selected from the group consisting of Methotrexate, Cytarabine, 5-fluorouracil, gemcitabine, 6-mercaptopurine, Fludarabine, Cladarabine, and Hydroxyurea, Alkylating agents selected from the group consisting of Cyclophosphamide, Ifosphamide, Chlorambucil, Melphalan, Temozolamide, Cisplatin, Carboplatin, and Oxaliplatin, Topoisomerase inhibitors selected from the group consisting of Irinotecan, Topotecan, Etoposide, and Teniposide, Mitotic inhibitors selected from the group consisting of Vincristine, Vinblastine, Vinorelbine, Docetaxel, and Paclitaxel, Antibiotics selected from the group consisting of Bleomycin, Actinomycin D, Doxorubicin, Daunorubicin, and Idarubicin, Protein kinase inhibitors selected from the group consisting of Imatinib, Dasatinib, Nilotinib, Erlotinib, Gefitinib, crizotinib, Dabrafenib, Vemurafenib, and Trametinib), Enzymes selected from L-Asparaginase, Proteasome inhibitors selected from the group consisting of Bortezomib and Carfilzomib), and Monoclonal antibodies selected from the group consisting of trastuzumab, bevacizumab, and rituximab.

14. The method of claim 4, further comprising treatment with an immunotherapy checkpoint inhibitor.

15. A kit, comprising a compound of claim 1, a container, and optionally instructions for the use there of.

* * * * *